US005789447A

United States Patent [19]

Wink, Jr. et al.

[11] Patent Number: 5,789,447
[45] Date of Patent: Aug. 4, 1998

[54] NITRIC OXIDE RELEASING COMPOUNDS AS PROTECTIVE AGENTS IN ISCHEMIA REPERFUSION INJURY

[75] Inventors: David A. Wink, Jr., Hagerstown; James B. Mitchell, Damascus; Angelo Russo, Bethesda; Murali C. Krishna, Derwood; Ingeborg Hanbauer, Chevy Chase, all of Md.; Matthew B. Grisham; Daniel Neil Granger, both of Shreveport, La.

[73] Assignees: The United States of America as represented by the Department of Health and Human Services, Washington, D.C.; The Board of Supervisors of Louisiana State University and Agricultural and Mechanical College, Baton Rouge, La.

[21] Appl. No.: 527,314

[22] Filed: Sep. 12, 1995

Related U.S. Application Data

[63] Continuation of Ser. No. 146,610, Nov. 2, 1993, abandoned.
[51] Int. Cl.⁶ .................................................... A61K 31/40
[52] U.S. Cl. .................................... 514/611; 514/642
[58] Field of Search ............................... 514/642, 611

[56] References Cited

U.S. PATENT DOCUMENTS 5,250,550  10/1993  Keefer et al. .......................... 514/357
5,714,511   2/1998  Saavedra et al. ....................... 514/426

OTHER PUBLICATIONS

Carey et al., Circulatory Shock, 38, 209–216 (1992).
Lefer et al., J. Cardiovasc. Pharmacol., 22 (Suppl. 7), S27–S33 (1993).
Lefer et al., Circulation, 88 (5 (1)), 2337–2350 (1993).
Masini et al., Biol. Nitric Oxide, Proc. 2nd Int. Meet. (Moncada, ed.), 1, 190–192 (1992).

Primary Examiner—Brian M. Burn
Attorney, Agent, or Firm—Leydig, Voit & Mayer, Ltd.

[57] ABSTRACT

The present invention provides a method for treating oxygen free radical induced tissue damage associated with ischemia reperfusion injury, wherein nitric oxide is delivered to target cells/tissues through the administration of a nitric oxide-containing compound that spontaneously releases nitric oxide under physiological conditions without requiring the presence of oxygen.

6 Claims, 16 Drawing Sheets

* p < 0.05 (Student's t-test)
† p < 0.005 (Student's t-test)

* p < 0.05 (Student's t-test)
† p < 0.005 (Student's t-test)

* p < 0.05 vs. Control group
† p < 0.005 vs. I/R untreated group

\* p < 0.05 as compared with the corresponding value before I/R

NITRIC OXIDE RELEASING COMPOUNDS AS PROTECTIVE AGENTS IN ISCHEMIA REPERFUSION INJURY

This is a continuation of copending application Ser. No. 08/146,610, now abandoned, filed on Nov. 2, 1993.

TECHNICAL FIELD OF THE INVENTION

The present invention is directed to a method of using nitric oxide-containing compounds that spontaneously release nitric oxide under physiological conditions without requiring the presence of oxygen to treat oxygen free radical mediated tissue damage associated with ischemia reperfusion injury.

BACKGROUND OF THE INVENTION

Oxygen free radicals, such as superoxide and peroxide, have been implicated in the genesis of many disease and degenerative states (Ames et al., *PNAS USA*, 78, 6858–6862 (1981); Halliwell et al., *FEBS*, 307, 108–112 (1992); Halliwell et al., *Arch. Biochem. Biophys.*, 246, 501–514 (1986); Halliwell et al., *Biochem. J.*, 219, 1–14 (1984); Minotti et al., *J. Biol. Chem.*, 262, 1098–1104 (1987)). For example, oxygen-mediated biological damage has been a mechanism involved in inflammation, ischemia reperfusion injury, stroke, rheumatoid arthritis, atherosclerosis, cancer, and aging. The chemistry of oxygen-mediated biological damage involves the Haber-Weiss cycle, in which Fenton-type intermediates, i.e., combinations of peroxide and metal, are generated:

$$O_2 + Fe^{2+} \rightarrow O_2^- + Fe^{3+}$$

$$O_2^- + Fe^{2+} \rightarrow H_2O_2 + Fe^{3+}$$

$$Fe^{2+} + H_2O_2 \rightarrow oxidant$$

oxidant+biological molecule→damage (Minotti et al. (1987), supra; Halliwell et al. (1992), supra). Study of mammalian (Mitchell et al., *Biochem.*, 29, 2802–2807 (1990)) and bacterial (Imlay et al., *Science*, 240, 640–642 (1988)) cell cultures has revealed that the primary cytotoxic agent is peroxide (Mitchell et al., supra), the major source of which is an extracellular superoxide and peroxide generating system involving hypoxanthine (HX) and xanthine oxidase (XO).

Intravital microscopic studies of tissues exposed to ischemia and reperfusion have revealed an acute inflammatory response that is characterized by enhanced protein efflux and increased adherence and emigration of leukocytes in postcapillary venules (Oliver et al., *Inflammation*, 15, 331–346 (1991); Lehr et al., *J. Clin. Invest.*, 87, 2036–2041 (1991); Messmer et al., *Adv. Exp. Med. Biol.*, 242, 95 (1988); and Yasahara et al., *Am. J. Physiol.*, 261, H1626–H1629 (1991)). NO has been shown to block platelet aggregation (Rubanyi et al., *Biochem. Biophys. Res. Comm.*, 181, 1392–1397 (1991)) and reduce platelet adhesion to endothelial cell monolayers (Radomski et al., *Lancet*, 2, 1057–1058 (1987)). Leukocyte-endothelial cell adhesive interactions in postcapillary venules has been inhibited by NO (Kubes et al., *PNAS USA*, 88, 4651–4655 (1991)) and inhibition of NO production increases microvascular permeability in cat small intestine (Kubes et al., *Am. J. Physiol.*, 262 (Heart Circ. Physio. 31), H611–H615 (1992a)). NO also has been reported to modulate protein extravasation in rat coronary (Filep et al., *Br. J. Pharmacol.*, 108, 323–326 (1993)) and intestinal (Hutcheson et al., *Br. J. Pharmacol.*, 101, 815–820 (1990)) circulation treated with proinflammatory mediators. In addition, diminished basal NO release after myocardial ischemia and reperfusion has been shown to promote neutrophil adherence to cat coronary endothelium. Whole organ studies have demonstrated an accumulation of neutrophils in postischemic tissues (Romson et al., *Circulation*, 67, 1016–1023 (1983); Simpson et al., *J. Clin. Invest.*, 81, 624–629 (1988); Smith et al., *Am. J. Physiol.*, 256, H789–H793 (1989); Entman et al., *FASEB J.*, 5, 2529–2537 (1991)), attenuation of ischemia-reperfusion-induced vascular injury in animals rendered neutropenic with neutrophil anti-serum (Simpson et al., supra; Hernandez et al., *Am. J. Physiol.*, 253, H699–H703 (1987); Carden et al., *Circ. Res.*, 66, 1436–1444 (1990)), and a reduction in reperfusion-induced vascular leakage by monoclonal antibodies which prevent leukocyte adhesion (Hernandez et al., supra; Carden et al., supra; Adkins et al., *J. Appl. Physiol.*, 69, 2012–2018 (1990)), all of which suggest a role for leukocytes as mediators of the microvascular dysfunction elicited by ischemia reperfusion. Such studies have also led to the recognition that leukocyte-endothelial cell adhesion may be a rate-limiting step in the pathogenesis of ischemia-reperfusion-induced tissue injury. In general, ischemia and reperfusion of mucosa and microvasculature result in increased mucosal permeability, leukocyte-endothelial cell adhesion, increased vascular permeability, platelet aggregation, and vascular thrombosis (Siegfried et al., *Am. J. Physiol.*, 263 (Heart Circ. Physiol. 32), H771–H777 (1992); Kubes, *Am. J. Physiol.*, 262 (Gastrointest. Liver Physiol. 25), G1138–G1142 (1992b); and Kubes et al., (1992a), supra). Endothelial dysfunction and parenchymal tissue injury produced by ischemia reperfusion has been reviewed along with pharmacological agents known to exert protective effects (Lefer et al., *Annu. Rev. Pharmacol. Toxicol* 31, 71–90 (1993)).

NO in high concentration has been suggested as a cytotoxic agent in ischemia reperfusion injury (Beckman, *Nature*, 345, 27–28 (1990)) and neurotoxicity (Dawson et al., *PNAS USA*, 88, 7797–7801 (1991)). The NO has been proposed to react with superoxide or peroxide generated by endogenous hypoxanthine/xanthine oxidase to form peroxynitrite anion, OONO⁻ (Beckman, supra), which has been invoked as a mediator in ischemia reperfusion injury (Beckman, supra) and lipid peroxidation (Radi et al., *Arch. Biochem. Biophys.*, 288, 481–487 (1991)) and as a primary cytotoxic agent generated by macrophages (Beckman et al., *PNAS USA*, 87, 1620–1624 (1990)).

Based on evidence that nitric oxide synthase (NOS) inhibitors increase tissue damage during in vivo ischemia reperfusion within the cerebral cortex and that nitric oxide prevents damage during ischemia reperfusion events in the brain and heart, it has been suggested that NO can also function as a cytoprotective agent (Johnson et al., *Critical Care Medicine*, 19, 244–252 (1991); Morikawa et al., *Am. J. Physiol.*, 263, H1632–H1635 (1992); Masini et al., *Agents and Actions*, 33, 53–56 (1991); Siegfried et al., *J. Pharm. Expt. Ther.*, 260, 668–675 (1992); Gambassi et al., *Pharmacol. Res.*, 25, 11–12 (1992); and Linz et al., *J. Mol. Cell Cardiol.*, 24, 909–919 (1992)). Primary neuronal cell cultures exposed to concentrations of NO as high as 1 mM show no adverse effects (Hanbauer et al., *Neuroreports*, 3, 409–412 (1992); Kiedrowski et al., *Mol. Pharmacol.*, 41, 779–784 (1992)). Administration of a NO-generating compound, such as nitroglycerin or nitroprusside, has been described to reduce NMDA receptor-mediated neuronal damage (U.S. Pat. No. 5,234,956). However, such compounds suffer from the disadvantages of metabolic as opposed to spontaneous release of NO and slow release rates (Lipton et al., *Nature*, *364*, 626–630 (1993)). The nitrone DMPO has been shown to reduce neuronal cell death more efficiently than the nitric oxide synthase inhibitor L-N-nitroarginine (Lafon-Cazal et al., *Nature*, 364, 535–537 (1993)). Additional studies have shown that NO, though present, plays only a minimal role in the pathological effects associated with ischemia reperfusion injury (Woditsch et al., *Am. J. Physiol.*, 263, H1390–H1396 (1992); Jaescheke et al., *Life Sciences*, 50, 1797–1804 (1992)) or tumor necrosis factor (TNF) mediated cytotoxicity (Fast et al., *J. Leukoc. Biol.*, 52, 255–261 (1992)). In fact, many of the biological events in which NO has been proposed as a toxin occur concurrently with the production of reactive oxygen species, e.g., immune responses and ischemia reperfusion injury. Reactive oxygen metabolites and granulocyte activation have been implicated in the ischemia-reperfusion-induced microvascular injury (Granger, *Am. J. Physiol.*, 255, H1269–H1275 (1988)).

In view of these reports, nitric oxide and nitrovasodilators, such as sodium nitroprusside and SIN-1, have been suggested to protect against ischemia reperfusion injury (Aoki et al., *Am. J. Physiol.*, 258 (Gastrointest. Liver Physiol. 21), G275–G281 (1990); Kubes et al., *Gastroenterology*, 104 (4 Suppl.), Abstract 728 (1993); Andrews et al., *Gastroenterology*, 104 (4 Suppl.), Abstract A33 (1993); Masini, supra; Masini et al., *Int. Arch. Allergy Appl. Immunol.*, 94, 257–258 (1991); and Johnson, supra). The protective role of nitric oxide has been supported by a showing that nitric oxide could quench Fenton-type oxidation (Kanner et al., *Arch. Biochem. Biophys.*, 289, 130–136 (1991)).

An attempt to provide nitric oxide in vivo involved the administration of high concentrations of nitric oxide in the gas phase. However, such a method damages lung tissue and results in the destruction of the nitric oxide by various chemical reactions, such as the diffusion-controlled oxidation of oxyhemoglobin in the blood, before it reaches the target cells or tissues.

In view of the disadvantages inherent in methods of treating oxygen-free radical mediated tissue damage associated with ischemia reperfusion which utilize nitric oxide gas or nitric oxide-containing compounds that do not spontaneously release NO in the presence or absence of oxygen, it is an object of the present invention to provide a method of treating oxygen free radical mediated tissue damage which overcomes the disadvantages of other methods. It is a related object of the present invention to provide a method of delivering nitric oxide to cells at risk of being injured or injured by ischemia reperfusion. It is another object of the present invention to provide a method of delivering nitric oxide to cells at risk of being injured or injured by ischemia reperfusion by means of an agent, in particular a water-soluble agent, that spontaneously releases NO under physiological conditions in the presence or absence of oxygen. It is a further object of the present invention to provide for such delivery in a controlled and predictable manner. These and other objects and advantages of the present invention, as well as additional inventive features, will be apparent from the description of the invention provided herein.

BRIEF SUMMARY OF THE INVENTION

The present invention provides a method of treating oxygen free radical mediated tissue damage associated with ischemia reperfusion injury, including that associated with transplantation, trauma, inflammation, stroke, seizure, rheumatoid arthritis, atherosclerosis, cancer, dementia, diabetes, hypertensive crisis, ulcers, lupus, sickle cell anemia, ischemic bowel syndrome, pulmonary emboli, Ball's syndrome, pancreatitis, heart attack, and aging. In the method, nitric oxide is delivered to target cells in a controlled and predictable manner through the administration of a nitric oxide-containing compound. The nitric oxide-containing compound spontaneously releases nitric oxide under physiological conditions in the presence or absence of oxygen.

DETAILED DESCRIPTION OF THE PREFERRED EMBODIMENTS

Figure 1A:
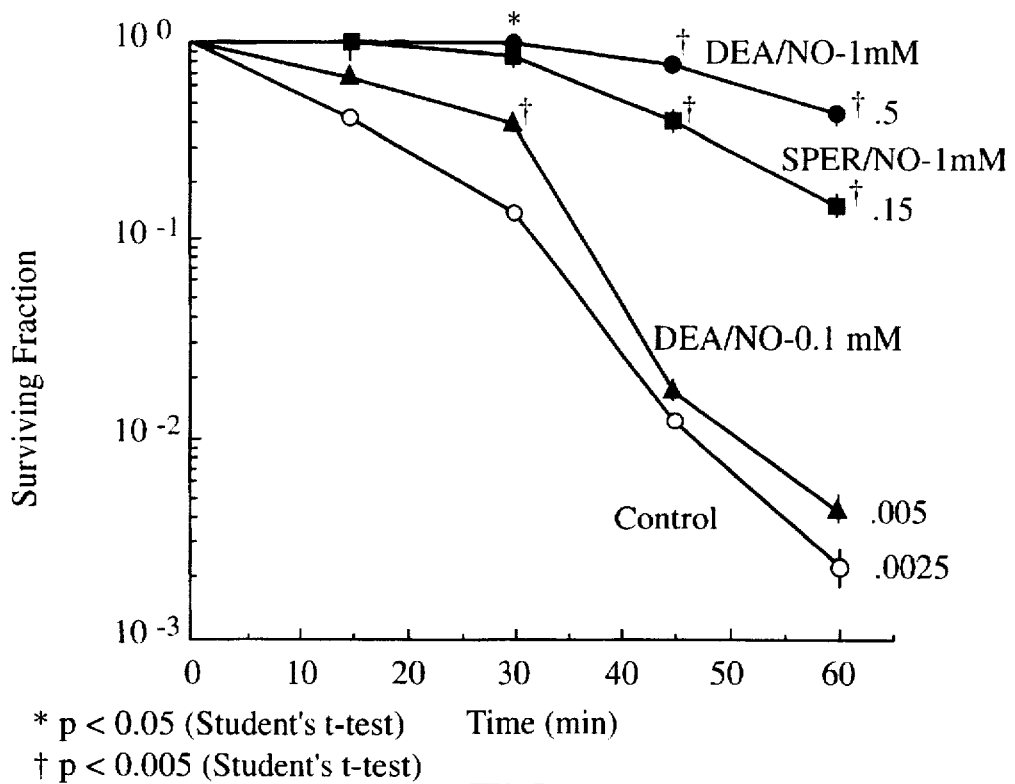
FIG. 1A is a graph of log of surviving fraction versus time (min) of exposure of cells to hypoxanthine/xanthine oxidase in the presence and absence of a nitric oxide-releasing compound.

It has been discovered, surprisingly, that nitric oxide-containing compounds that spontaneously release NO under physiological conditions without requiring the presence of oxygen can be used to treat oxygen free radical mediated tissue damage associated with ischemia reperfusion injury. The present invention thus provides a method of treating oxygen free radical mediated tissue damage associated with ischemia reperfusion injury. In accordance with the method of the present invention a nitric-oxide containing compound is administered to a mammal at risk for or having ischemia reperfusion injury in an amount sufficient to treat oxygen free radical mediated tissue damage associated with ischemia reperfusion injury. The nitric oxide-containing compounds used in the present inventive method spontaneously release nitric oxide under physiological conditions in the presence or absence of oxygen.

In keeping with the present invention, a series of amine derivatives of dimeric nitric oxide (NONOates) are particularly useful. The NONOates have been shown to release nitric oxide in a predictable manner under physiological conditions (Maragos et al., *J. Med. Chem.*, 34, 3242–3247 (1991)). The half-lives of the NONOates can range from 1 minute to several days (Hrabie et al., *J. Org. Chem.*, 58, 1472–1476 (1993)) and, accordingly, offer advantages over compounds, such as spermidine and spermine, by having characteristically prolonged half-lives in solution. The NONOates have been employed in various studies of cytostasis (Maragos et al., *Cancer Res.*, 53, 564–568 (1993)), cytotoxicity, mutagenicity (Wink et al., *Science*, 254, 1001–1003 (1991)), nitric oxide-mediated dopamine release in nerve cell cultures, and nitric oxide-mediated inhibition of platelet aggregation (Keefer et al., in *Biology of Nitric Oxide, 2, Enzymology, Biochemistry, Immunology*, Moncada et al., eds., Portland Press, Chapel Hill, N.C., pages 153–156, (1992)). Vasorelaxation of aortic ring strips was shown to correlate linearly to the concentration of nitric oxide release from the NONOates (Maragos et al., supra). NONOates also have been shown to be effective in the treatment of cardiovascular disorders and hypertension (U.S. Pat. Nos. 4,954,526, 5,155,137, and 5,212,204 and WO 93/07114) and have been suggested to be effective in cancer chemotherapy (Maragos et al. (1993), supra). The potential utility of the NONOates in other biomedical applications also has been suggested (Maragos et al. (1991), supra; Keefer et al.(1992), supra).

Several types of NONoates are useful in the method of the present invention. One type of NONOates useful for treating oxygen free radical mediated tissue damage associated with ischemia reperfusion injury in a mammal are NONOates of the formula:

[R₁N(R₂)N(NO)O]ᵧX    (Formula I)

wherein $R_1$ and $R_2$ are the same or different and are selected from the group consisting of hydrogen, a $C_1$–$C_8$ alkyl, a $C_6$–$C_{10}$ aryl, a $C_4$–$C_{10}$ heterocyclic nitrogen-containing radical, a $C_6$–$C_{10}$ aryl substituted with a $C_1$–$C_3$ alkyl, and a $C_3$–$C_{10}$ cycloalkyl, either or both of which R groups may be substituted by 1–3 substituents, which may be the same or different and are selected from the group consisting of halo, hydroxy, $C_1$–$C_8$ alkoxy, amino, amido, formyl, carboxy, and nitro, with the proviso that both $R_1$ and $R_2$ cannot be hydrogen; and wherein X is a pharmaceutically acceptable cation, a pharmaceutically acceptable metal center, or a pharmaceutically acceptable organic group selected from the group consisting of a $C_1$–$C_8$ alkyl, acyl, and amido; and wherein Y is 1 to 3 and is consistent with the valence of X, sufficient to treat the oxygen free radical mediated tissue damage.

The term "$C_1$–$C_8$ alkyl" is used to refer to branched and straight chain hydrocarbon radicals of 1–8 carbons, such as methyl, ethyl, propyl, isopropyl, butyl, 2-butyl, tert-butyl, amyl, isoamyl, hexyl, heptyl, octyl, and the like. The term "$C_6$–$C_{10}$ aryl" is used to refer to aromatic cyclic hydrocarbon radicals of 6–10 carbons, such as phenyl, naphthyl and the like, and the term "$C_4$–$C_{10}$ heterocyclic nitrogen-containing radical" is used to refer to radicals such as pyrrolyl, pyridinyl, quinolinyl, isoquinolinyl, and the like. Similarly, "$C_3$–$C_{10}$ cycloalkyl" is used to refer to nonaromatic cyclic hydrocarbon radicals of 3–10 carbons, such as cyclopropyl, cyclopentyl, cyclohexyl, cycloheptyl, cyclooctyl, and the like. The terms "halo" and "halogen" are intended to include fluorine, chlorine, bromine, and iodine. Other terms should be given those meanings normally ascribed to such terms by those of skill in the art.

The term "pharmaceutically acceptable cation" as used herein means any cation biologically compatible in a mammal and includes alkylammonium cations, e.g., isopropyl ammonium cation and the like; alkali metals, e.g., sodium, potassium, lithium, and the like; and alkaline earth metals, e.g., calcium, barium, magnesium, and the like. The only essential characteristic of the cation chosen is that it not be biologically incompatible in a mammal.

The term "pharmaceutically acceptable metal center" as used herein means a central metal ion, having a valence of 1 to 3 attached by coordinate links to one or more nonmetal atoms of each of the Y organic groups of the above formula. The term "central metal ion" as used herein includes biologically acceptable metal ions selected from alkali metals, such as sodium, potassium, lithium, and the like; alkaline earth metals, such as calcium, magnesium, barium, and the like; transition metals, including iron, copper, nickel, zinc, and the like; Group III metals including aluminum and the like, and lanthanide series metals. The only principal requirement for the central metal ion chosen is biological compatibility in a mammal.

The term "pharmaceutically acceptable organic group" as used herein refers to those biologically acceptable organic groups that covalently bond to the organic grouping of the compound of the above formula to form ethers and other derivatives thereof. Acceptable organic groups include lower alkyls, acyl, amido, and the like.

Additional types of nitric oxide-releasing compounds useful in the method of the present invention include the nitric oxide-releasing NONOates of Formulas II, III and IV:

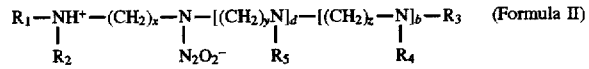    (Formula II)

or

    (Formula III)

or

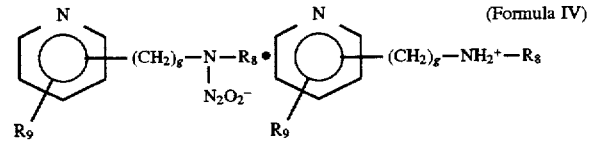    (Formula IV)

wherein b and d are independently zero or one; x, y, and z are independently 2–12; $R_1$–$R_8$ are independently hydrogen, $C_3$–$C_8$ cycloalkyl, $C_1$–$C_{12}$ straight or branched chain alkyl, benzyl, benzoyl, phthaloyl, acetyl, trifluoroacetyl, p-toluyl, t-butoxycarbonyl or 2,2,2-trichloro-t-butoxycarbonyl; $R_9$ is hydrogen or a $C_1$–$C_{12}$ straight or branched chain alkyl; B is

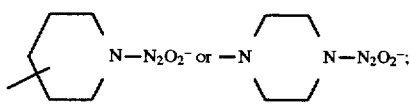

f is 0–12, with the proviso that when B is the substituted piperazine moiety

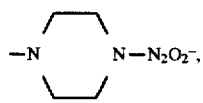

then f is 2–12; and g is 2–6. The group —$N_2O_2^-$ has the structure

Preferred among the compounds of Formulas II and III are those compounds wherein $R_1$–$R_7$ are independently hydrogen, $C_{3-8}$ cycloalkyl, $C_{1-12}$ straight or branched chain alkyl, benzyl, or acetyl. More preferred are those compounds wherein $R_1$–$R_7$ are independently hydrogen, methyl, ethyl, benzyl or acetyl, and x, y and z are 2–4. Most preferred are those compounds wherein $R_1$–$R_7$ are independently hydrogen, methyl, benzyl or acetyl, and x, y and z are 2–4.

Preferred among the compounds of Formula IV are those compounds wherein $R_8$ is $C_{5-6}$ cycloalkyl, $C_{1-4}$ straight or branched chain alkyl, benzyl or acetyl. More preferred are those compounds wherein $R_8$ is methyl, ethyl, benzyl or acetyl, and most preferred are those compounds wherein $R_8$ is methyl or acetyl.

In addition to the nitric oxide-releasing compounds of Formulas I-IV, the following nitric oxide-releasing compounds of the Formula V, VI, VII and VIII are useful in the present inventive method as follows:

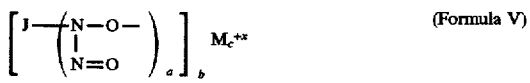
(Formula V)

wherein J is an organic or inorganic moiety, preferably a moiety which is not linked to the nitrogen of the $N_2O_2$ group through a carbon atom, $M_c^{+x}$ is a pharmaceutically acceptable cation, where x is the valence of the cation, a is 1 or 2, and b and c are the smallest integers that result in a neutral compound, preferably such that the compound is not a salt of alanosine or dopastin, as described in U.S. Pat. No. 5,212,204;

(Formula VI)

wherein $R_1$ and $R_2$ are independently selected from the group consisting of a straight chain or branched chain $C_1$–$C_{12}$ alkyl group and a benzyl group, or else $R_1$ and $R_2$ together with the nitrogen atom are bonded to form a heterocyclic group, preferably a pyrrolidino, piperidino, piperazino or morpholino group, $M^{+x}$ is a pharmaceutically acceptable cation, and x is the valence of the cation, as described in U.S. Pat. No. 5,039,705;

$K[(M)^{x'}_x(L)_y(R^1R^2N—N_2O_2)_z]$ (Formula VII)

wherein M is a pharmaceutically acceptable metal, or, where x is at least two, a mixture of two different pharmaceutically acceptable metals, L is a ligand different from ($R^1R^2N$—$N_2O_2$) and is bound to at least one metal, $R^1$ and $R^2$ are each organic moieties and may be the same or different, x is an integer of from 1 to 10, x' is the formal oxidation state of the metal M, and is an integer of from 1 to 6, y is an integer of from 1 to 18, and where y is at least 2, the ligands L may be the same or different, z is an integer of from 1 to 20, and K is a pharmaceutically acceptable counterion to render the compound neutral to the extent necessary, as described in U.S. patent application Ser. No. 07/858,885, filed Mar. 27, 1992; and

(Formula VIII)

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo or benzyl, or $R_1$ and $R_2$ together with the nitrogen atom to which they are bonded form a heterocyclic group, preferably a pyrrolidino, piperidino, piperazino or morpholino group, and $R_3$ is a group selected from $C_{1-12}$ straight chain and $C_{3-12}$ branched chain alkyl which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_{1-12}$ unsubstituted or substituted acyl, sulfonyl and carboxamido; or $R_3$ is a group of the formula —$(CH_2)_n$—ON=N(O)$NR_1R_2$, wherein n is an integer of 2–8, and $R_1$ and $R_2$ are as defined above; with the proviso that $R_1$, $R_2$ and $R_3$ do not contain a halo or a hydroxy substituent α to a heteroatom, as described in U.S. patent application Ser. No. 07/950,637, filed Sep. 22, 1992.

In addition to the nitric oxide-releasing compounds described above, other nitric oxide-containing compounds that spontaneously release NO under physiological conditions and do not require the presence of oxygen can be used in the present inventive method. These compounds include S-nitroso adducts of the formula O=N—S—R, wherein R is selected from the group consisting of a $C_1$–$C_8$ alkyl, a $C_6$–$C_{10}$ aryl, a $C_4$–$C_{10}$ heterocyclic nitrogen-containing radical, a $C_6$–$C_{10}$ aryl substituted with a $C_1$–$C_3$ alkyl, and a $C_3$–$C_{10}$ cycloalkyl, which R groups may be substituted by 1–3 substituents, which may be the same or different and are selected from the group consisting of halo, hydroxy, $C_1$–$C_8$ alkoxy, amino, amido, formyl, carboxy, and nitro. Preferred S-nitroso adducts include S-nitroso adducts of peptides and proteins, particularly S-nitroso-N-acetyl penicillamine (SNAP) (Morley et al., *J. Cardiovasc. Pharmacol.*, 21, 670–676 (1993); Feelisch, *J. Cardiovasc. Pharmacol.*, 17, S25–S33 (1991); Stamler et al., *PNAS (USA)*, 89, 7674–7677 (1992); and Stamler et al., *PNAS (USA)*, 89, 444–448 (1992)). Such adducts offer the advantages of cell-targeting methods, through the use of adducts of S-nitroso cell-specific antibodies and adducts of S-nitroso peptides that mimic recognition sequences of receptor ligands.

The compounds used in the present inventive method are characterized in that they are highly soluble in physiological solutions and release NO spontaneously without the need for enzymatic conversion. The release of NO, in particular the rate of release, can be controlled by the choice of the nucleophile moiety, is independent of the presence of oxygen, and is not accompanied by overtly toxic byproducts.

The compounds used in the present inventive methods may be synthesized according to methods that are well known in the art. It is preferred that appropriate amines be obtained from suitable commercial suppliers and reacted with nitric oxide under suitable conditions to obtain the desired compound. Suitable commercial suppliers include, among others, Aldrich Chemical Co., Milwaukee, Wis.

Once a suitable amine has been synthesized or otherwise obtained (e.g., from a commercial supplier), it may then be reacted with nitric oxide to obtain a compound for use in the present invention. For example, one of the methods of Drago et al., *J. Am. Chem. Soc.*, 83, 1819–1822 (1961), may be used to react a suitable primary amine with nitric oxide. Certain diamines may be prepared in accordance with Garrido et al., *J. Org. Chem.*, 49, 2021–2023 (1984). Certain triamines may be prepared in accordance with Bergeron, *Accts. Chem. Res.*, 19, 105–113 (1986). Bergeron, in *J. Ore. Chem.*, 53, 3108–3111 (1988), also describes various methods that may be used to prepare tetraamines. Carboni et al., *Tet. Let.*, 29, 1279–1282 (1988), discloses techniques that are relevant to the preparation of di-, tri-, and tetraamines. Other methods that may be employed in synthesis are described in U.S. Pat. Nos. 4,954,526 and 5,155,137.

Once a suitable amine has been prepared or commercially obtained, it may then be reacted with nitric oxide to produce one of the nitric oxide-containing compounds to be used in the present inventive methods. Suitable methods are described in the '526 and '137 patents, for example. If certain of the amines to be reacted with nitric oxide contain additional nitrogen, oxygen, or other heteroatoms, suitable blocking groups may be employed to prevent the reaction of such atoms with nitric oxide. The blocked heteroatoms may then be unblocked after the Drago reaction of the amine with nitric oxide. Such blocking/deblocking agents and methods of using them are known in the art.

Once the desired nitric oxide adduct has been prepared, a pharmaceutically acceptable salt thereof can be prepared, if desired. For example, the potassium salt of the compound can be prepared by reacting the compound with potassium hydroxide in ethanol or similar solution. Alternatively, sodium, calcium, and magnesium salts, among others, can be prepared.

The nitric-oxide releasing compounds can be used in the method of the present invention in many forms, including by way of illustration as the compounds per se or in the form of their pharmaceutically acceptable salts and derivatives. The compounds can be used alone or in appropriate combination with one or more other compounds/derivatives of nitric-oxide releasing compounds or with other active compounds. It should be understood, however, that the salt or derivative should not be one that renders the compound unstable or insoluble in water or toxic at the doses contemplated.

S-nitroso adducts of peptides and proteins form readily as described in the art. See, for example, the two papers by Stamler et al., supra.

The nitric-oxide releasing compounds can also be incorporated into a polymeric matrix as described in U.S. patent application Ser. No. 07/935,565. Incorporation of the $N_2O_2^-$ functional group into a polymeric matrix provides a polymer-bound nitric oxide/nucleophile adduct composition that can be applied with specificity to a biological target site. Site-specific application of a polymer-bound adduct enhances the selectivity of action of the nitric oxide releasing $N_2O_2^-$ functional group. If $N_2O_2^-$ functional groups attached to the polymer are necessarily localized, then the effect of their nitric oxide release will be concentrated in the tissues with which they are in contact. If the polymer is soluble, selectivity of action can still be arranged, for example, by attachment to or derivatization of an antibody specific to the target tissue. Similarly, attachment of $N_2O_2^-$ groups to small peptides that mimic the recognition sequences of ligands for important receptors provides localized concentrated effect of nitric oxide release, as would attachment to oligonucleotides capable of site-specific interactions with target sequences in a nucleic acid.

Additionally, incorporation of the $N_2O^{2-}$ functional group into a polymer matrix can reduce the propensity of the nitric oxide/nucleophile adduct for the relatively rapid release of nitric oxide. This prolongs the release of nitric oxide by the $N_2O_2^-$ functional group, and allows for efficient dosing to achieve a desired biological effect so the frequency of dosing can be reduced.

While not being bound to any particular theory, it is believed that longevity of nitric oxide release in the polymer-bound nitric oxide/nucleophile adduct compositions of the present invention is to be attributed both to the physical structure of the composition and to electrostatic effects. Thus, it is believed that if the polymer is an insoluble solid, $N_2O_2^-$ groups near the surface of the particle should be available for rapid release while those that are more deeply imbedded are sterically shielded, requiring more time and/or energy for the nitric oxide to work its way into the medium. Unexpectedly, it has been found that increasing positive charge in the vicinity of an $N_2O_2^-$ functional group also tends to increase the half-life of nitric oxide generation. The mechanism of this rate retardation may be attributable simply to repulsive electrostatic interactions, i.e., increasing the number of $H^+$-repelling positive charges in the vicinity of the $N_2O_2^-$ groups inhibits attack of positively charged $H^+$ ions on the $N_2O_2^-$ functional group and slows the rate of its $H^+$- catalyzed decomposition. For example, by attaching amino groups to the polymeric support that are capable of forming the nitric oxide-releasing $N_2O_2^-$ functional group on reaction with nitric oxide, partially converted structures can be produced on less-than-exhaustive treatment with nitric oxide that after exposure to water contain a large number of positively charged ammonium centers surrounding the $N_2O_2^-$ group that electrostatically inhibit the approach of $H^+$ ions capable of initiating nitric oxide loss from the nitric oxide releasing $N_2O_2^-$ functional group.

The nitric oxide-releasing $N_2O_2^-$ functional groups that are bound to the polymer generally are capable of releasing nitric oxide in an aqueous environment spontaneously upon contacting an aqueous environment, i.e., they do not require activation through a redox reaction or electron transfer such as is required for glyceryl trinitrate and sodium nitroprusside. Some of the nitric oxide/nucleophile complexes useful in the context of the present invention do require activation by particular means, but only as necessary to free the nitric oxide releasing X[N(O)NO]$^-$ group in the vicinity of the particular cells of interest. As an example, covalent attachment of a protecting group to the anionic |N(O)NO|$^-$ function provides a means of postponing nitric oxide release until the molecule reaches an organ capable of metabolically removing the protecting group. By choosing a protecting group that is selectively cleaved by enzymes specific to a cell or tissue of interest, for example, the action of the nitric oxide/nucleophile complex can be targeted to maximize the desired effect. While the polymer-bound nitric oxide releasing compositions of the present invention are capable of releasing nitric oxide in an aqueous solution, such a compound preferably releases nitric oxide under physiological conditions.

The nitric oxide releasing $N_2O_2$ functional group for attachment to a polymer is preferably a nitric oxide/nucleophile adduct, e.g., a complex of nitric oxide and a nucleophile, most preferably a nitric oxide/nucleophile complex which contains the anionic moiety $X[N(O)NO]^-$, where X is any suitable nucleophile residue. The nucleophile residue is preferably that of Formula I, such as a primary (e.g., $X=(CH_3)_2CHNH$, as in $(CH_3)_2CHNH[N(O)NO]Na$) or secondary amine (e.g., $X=(CH_3CH_2)_2N$, as in $(CH_3CH_2)_2N[N(O)NO]Na$), or a polyamine (e.g., X=spermine, as in the zwitterion $H_2N(CH_2)_3NH_2^+(CH_2)_4N[N(O)NO]^-(CH_2)_3NH_2$, or X=3-(n-propylamino) propylamine, as in the zwitterion $CH_3CH_2CH_2N[N(O)NO]^-CH_2CH_2CH_2NH_3^+$), or a derivative thereof. Such nitric oxide/nucleophile complexes are stable solids and are capable of delivering nitric oxide in a biologically usable form at a predictable rate.

The nucleophile residue for polymer attachment is preferably not an entity such as that of sulfite (e.g., $X=SO_3$, as in $NH_4O_3S[N(O)NO]NH_4$) even though the complex is a stable compound, since it is capable of releasing nitric oxide in an aqueous environment only under harsh, nonphysiological conditions.

Other suitable nitric oxide/nucleophile complexes for attachment to a polymer include those having the formulas of Formulas II–VIII above.

Any of a wide variety of polymers can be used to make polymer NONOates. It is only necessary that the polymer selected is biologically acceptable. Illustrative of polymers suitable for use in the present invention are polyolefins, such as polystyrene, polypropylene, polyethylene, polytetrafluorethylene, polyvinylidene difluoride, polyvinylchloride, derivatized polyolefins such as polyethylenimine, polyethers, polyesters, polyamides such as nylon, polyurethanes, biopolymers such as peptides, proteins, oligonucleotides, antibodies and nucleic acids, starburst dendrimers, and the like.

The physical and structural characteristics of the polymers suitable for use in the present invention are not narrowly critical, but rather will depend on the end use application. It will be appreciated by those skilled in the art that where the polymer-bound nitric oxide/nucleophile adduct compositions of the present invention are intended for topical, dermal, percutaneous, or similar use, they need not be biodegradable. For some uses, such as ingestion or the like, it may be desirable that the polymer of the polymer-bound compositions slowly dissolves in a physiological environment or that it is biodegradable.

The nitric oxide-releasing complexes having $N_2O_2^-$ functional groups, including the compounds described above, may be bound to the polymer support in a number of different ways. For example, the compounds described above may be bound to the polymer by coprecipitation of such compounds with the polymer. Coprecipitation involves, for example, solubilizing both the polymer and the nitric oxide/nucleophile compound and evaporating the solvent.

Alternatively, nitric oxide releasing $N_2O_2^-$ functional groups may be bound to the polymer by formation of a nitric oxide/nucleophile complex of the types and having the formulas of those described above, in situ on the polymer. The $N_2O_2^-$ functional group may be attached to an atom in the backbone of the polymer, or it may be attached to a group pendant to the polymer backbone, or it may simply be entrapped in the polymer matrix. Where the $N_2O_2^-$ functional group is in the polymer backbone, the polymer includes in its backbone sites which are capable of reacting with nitric oxide to bind the nitric oxide for future release.

For example, where the polymer is polyethylenimine, the polymer includes nucleophilic nitrogen atoms which react with nitric oxide to form the $N_2O_2^-$ functional group at the nitrogen in the backbone. Where the $N_2O_2^-$ functional group is a group pendant to the polymer backbone, the polymer contains, or is derivatized with, a suitable nucleophilic residue capable of reacting with nitric oxide to form the $N_2O_2^-$ functionality. Reaction of the polymer which contains a suitable nucleophilic residue, or of the suitably derivatized polymer with nitric oxide thus provides a polymer-bound nitric oxide-releasing $N_2O_2^-$ functional group. To form the polymer-bound nitric oxide releasing $N_2O_2^-$ functional group, it is generally preferred to impart a net charge to the polymer near the site on the polymer where the $N_2O_2^-$ functional group is to be formed. The resulting polymer bound nitric oxide-releasing compounds may then be administered as described below or may be formed into an implant for implantation in or near a site of ischemia reperfusion injury for example.

The present inventive methods can be utilized in vitro for scientific and research purposes. However, the methods of the present invention have particular usefulness in in vivo applications, such as treating oxygen free radical mediated tissue damage associated with ischemia reperfusion injury. "Treating" means protecting against the onset of oxygen free radical mediated tissue damage, where the method is used prior to the onset of ischemia reperfusion, as well as protecting against further oxygen free radical mediated tissue damage, where ischemia reperfusion injury has already been initiated. The method is believed to accomplish the objective of treating oxygen free radical mediated tissue damage by intercepting reactive oxygen species or by forming metal nitrosyl complexes, which prevent formation of reactive oxygen species. The NO is also believed to increase blood flow in damaged tissue, thereby increasing oxygenation. Accordingly, the present inventive methods have both prophylactic and therapeutic benefits. The present invention includes the administration to a mammal, particularly a human, at risk for or having ischemia reperfusion injury an amount of one or more of the nitric-oxide releasing compounds previously described or pharmaceutically acceptable salts or derivatives thereof or polymers, alone or in combination with one or more other pharmaceutically active compounds, in a pharmaceutically acceptable composition sufficient to treat the oxygen free radical mediated tissue damage.

The nitric oxide-releasing compound or polymer preferably is administered as soon as possible after it has been determined that a mammal, particularly a human, is at immediate risk for ischemia reperfusion injury or has just begun to realize ischemia reperfusion injury. It is expected that, in most situations, the nitric oxide-releasing compound will be administered within about 15 minutes to about 60 minutes of injury, i.e., before or after injury as appropriate. When it is possible to predict the onset of ischemia reperfusion, e.g., associated with transplantation, the compound or polymer should be administered immediately upon knowledge of need. It is expected that, in such situations, the nitric-oxide-releasing compound will be administered within about 15 minutes before the onset of ischemia reperfusion. When ischemia reperfusion injury has already begun, the compound or polymer should be administered as soon as possible after the onset of ischemia reperfusion. It is expected that, in such situations, the nitric oxide-releasing compound will be administered within about 15 minutes to about 60 minutes after the onset of ischemia reperfusion. The term to treat the oxygen free radical mediated tissue damage will depend, in part, upon the particular nitric oxide-releasing compound or polymer used, the amount administered, the method of administration, and the cause and extent of oxygen free radical mediated damage anticipated or realized.

The present inventive method is useful in treating oxygen free radical mediated tissue damage associated with any condition or disease state associated with or characterized by ischemia reperfusion, wherein "ischemia," otherwise known as hypoemia, refers to a region of localized tissue anemia due to the obstruction of arterial blood flow to the region and wherein "reperfusion" refers to the restoration of blood flow to the ischemic region. Examples of such conditions and disease states include transplantation, trauma, inflammation, stroke, seizure, rheumatoid arthritis, atherosclerosis, cancer, dementia, diabetes, hypertensive crisis, ulcers, lupus, sickle cell anemia, ischemic bowel syndrome, pulmonary emboli, Ball's syndrome, pancreatitis, heart attack, and aging, for example. Accordingly, use of the term "ischemia reperfusion" is intended to encompass these and other conditions involving ischemia reperfusion.

One skilled in the art will appreciate that suitable methods of administering a nitric oxide-releasing compound useful in the method of the present invention to a mammal are available. Although more than one route can be used to administer a particular compound, a particular route can provide a more immediate and more effective reaction than another route. Accordingly, the described methods are merely exemplary and are in no way limiting.

The dose administered to an animal, particularly a human, in accordance with the present invention should be sufficient to effect the desired response, i.e., treatment of oxygen free radical mediated tissue damage, in the animal over a reasonable time frame. One skilled in the art will recognize that dosage will depend upon a variety of factors including the strength (i.e., nitric oxide release capability) of the particular compound employed, the age, species, condition or disease state, and body weight of the animal, as well as the amount of cells or tissue about to be affected or actually affected by ischemia reperfusion injury. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states, in particular chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of about 0.1 to about 100 mg of one or more of the compounds or polymers described above per kg body weight.

The present invention also provides a pharmaceutical composition comprising a pharmaceutically acceptable carrier and an amount of a nitric-oxide containing compound sufficient to treat oxygen free radical-mediated tissue damage. The carrier may be any of those conventionally used and is limited only by chemico-physical considerations, such as solubility and lack of reactivity with the compound, and by the route of administration. It will be appreciated by one of skill in the art that, in addition to the following described pharmaceutical composition, the compounds of the present inventive method may be formulated as inclusion complexes, such as cyclodextrin inclusion complexes, or liposomes.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulphonic, for example p-toluenesulphonic acids.

The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the active compounds and one which has no detrimental side effects or toxicity under the conditions of use.

The choice of excipient will be determined in part by the particular compound, as well as by the particular method used to administer the composition. Accordingly, there is a wide variety of suitable formulations of the pharmaceutical composition of the present invention. The following formulations for oral, aerosol, parenteral, subcutaneous, intravenous, intramuscular, interperitoneal, rectal, and vaginal administration are merely exemplary and are in no way limiting.

Injectable formulations are among those formulations that are preferred in accordance with the present inventive methods. The requirements for effective pharmaceutical carriers for injectable compositions are well known to those of ordinary skill in the art (See *Pharmaceutics and Pharmacy Practice*, J.B. Lippincott Company, Philadelphia, Pa., Banker and Chalmers, eds., pages 238–250, (1982), and *ASHP Handbook on Injectable Drugs*, Toissel, 4th ed., pages 622–630 (1986)). It is preferred that such injectable compositions be administered intravenously or locally, i.e., at or near the site of ischemia reperfusion injury.

Topical formulations are well-known to those of skill in the art and are suitable in the context of the present invention for application to skin and hair as radiation protection.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds or polymers of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the compounds and polymers useful in the present inventive methods may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The following examples further illustrate the present invention and, of course, should not be construed as in any way limiting its scope.

EXAMPLE 1

This example describes the treatment of peroxide-mediated cytotoxicity in Chinese hamster V79 fibroblasts by nitric-oxide containing compounds that spontaneously release nitric oxide under physiological conditions without requiring the presence of oxygen.

Chinese hamster V79 lung fibroblasts were cultured in F12 medium supplemented with 10% fetal calf serum and antibiotics. Cell survival was assessed by clonogenic assay with 85–95% plating efficiency. Stock cultures of exponentially growing cells were trypsinized, rinsed, and plated ($7\times10^5$ cells/dish) into a number of 100 $cm^2$ petri dishes and incubated 16 hr at 37° C. prior to experimental protocols.

V79 cells exposed to hydrogen peroxide or HX/XO have been shown to serve as a good model for the study of reactive oxygen species in events such as ischemia reperfusion (Mitchell et al., supra, Gelvan et al., *PNAS USA*, 88, 4680–4684 (1991)). It has been shown that exposure of V79 cells to hydrogen peroxide results in dose-dependent cytotoxicity (Mitchell et al., supra). HX/XO induced cytotoxicity was not treated by the addition of superoxide dismutase. In contrast, catalase addition treated the cytotoxicity, indicating that hydrogen peroxide was the predominant toxin (Mitchell et al., supra).

HX and XO were purchased from Boehringer Co. (Indianapolis, Ind.). Nitrite, diethylamine, sulfinamide, diethylenetriaminepentaacetic acid (DETAPAC) and N-(1-naphthyl)ethylenediaminedihydrogenchloride (NEDD) were purchased from Aldrich (Milwaukee, Wis.). Cytosine-β-D-arabinofuranoside and ferricytochrome c were purchased from Sigma (St. Louis, Mo.). DEA/NO and SPER/NO were synthesized as previously described (Maragos et al., (1991), supra).

Figure 1B:
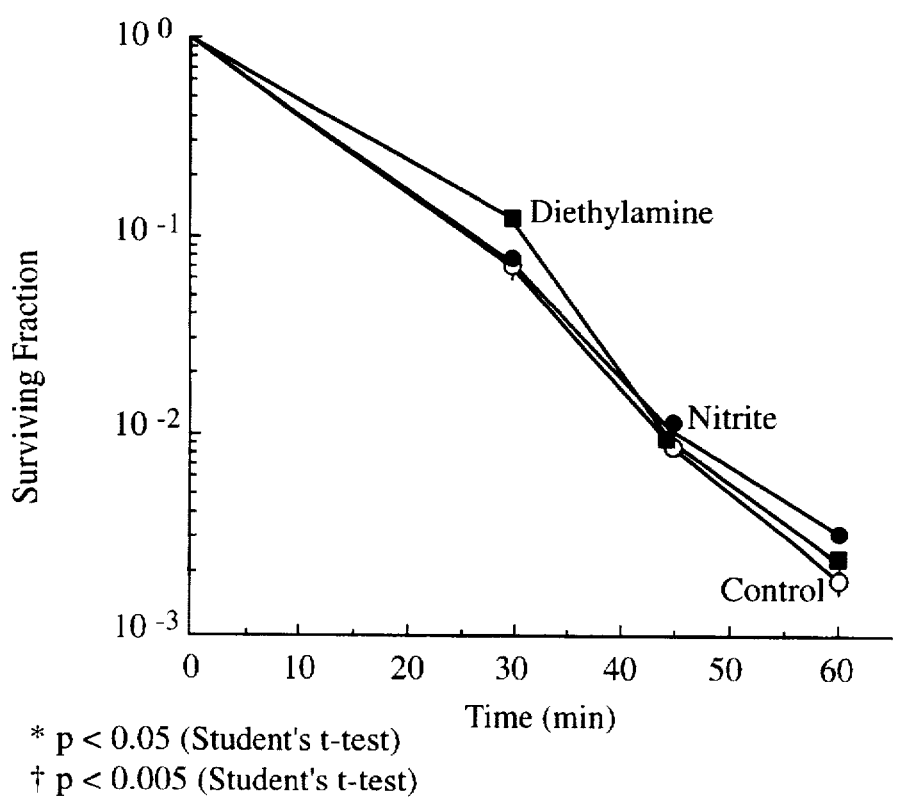
FIG. 1B is a graph of log of surviving fraction versus time (min) of exposure of cells to hydrogen peroxide in the presence and absence of DEA/NO breakdown products.

Exponentially growing cultures of Chinese hamster V79 fibroblasts were exposed to either HX/XO (final concentration of HX was 0.5 mM; 0.08 units/ml XO were used) for various amounts of time (FIG. 1A) or to various concentrations of hydrogen peroxide for one hour (FIG. 1B). DEA/NO, SPER/NO, nitrite, or diethylamine (final concentration of 1 mM) were added to parallel cultures immediately prior to addition of HX/XO or hydrogen peroxide. Additionally, 1 mM DEA/NO was added to medium in the absence of cells, incubated at 37° C. for 1 hr or 16 hrs, and then added just prior to the addition of hydrogen peroxide to evaluate the effects of DEA/NO which had released NO. After treatment, cell monolayers were rinsed twice with phosphate-buffered saline (PBS), trypsinized, counted and plated in triplicate for macroscopic colony formation. Each dose determination was plated in triplicate and experiments were repeated a minimum of two times. Plates were incubated for 7 days, after which colonies were fixed with methanol/acetic acid (3:1), stained with crystal violet, and counted. Colonies containing more than 50 cells were scored.

The activity of XO was monitored in the absence and presence of 1 mM DEA/NO by two different assays. Superoxide-induced reduction of ferricytochrome c to ferrocytochrome c was monitored spectrophotometrically at 550 nm (Fridovich, *Handbook of Method for Oxygen Radical Research*, pages 213–215 (1985)). The reaction was carried out in a 1 ml volume in aerated phosphate buffer (pH 7.8, 50 mM) containing 50 µM DETAPAC. HX was maintained at 2.5 mM and ferricytochrome c at 20 µM. The reactions were initiated with the addition of XO (final concentration of 0.2 units/ml). The activity of XO in the absence and presence of 1 mM DEA/NO was directly monitored by measuring the production of uric acid spectrophotometrically at 305 nm for 10 min under the same conditions but in the absence of ferricytochrome c. All enzymatic assays and chemical reactions were done at 37° C.

Anaerobic solutions of 1 mM hydrogen peroxide in 10 mM phosphate buffer, pH 7.4, were mixed with 1 mM NO. No rapid formation of nitrate/nitrite (<1000 s) was observed at 210 nm using stopped-flow techniques (Wink et al., *Chem. Res. Toxicol.*, 6, 23–27 (1993)). In addition, the nitrosation of sulfinamide in an aerobic solution (100 mM phosphate buffer, pH 7.4) by intermediates of the $NO/O_2$ reaction followed by subsequent diazotization with NEDD to form the azo dye was not inhibited in the presence of 1 mM hydrogen peroxide; thus, the consumption of NO by hydrogen peroxide was not significant under these conditions. The rate of decomposition of DEA/NO was unaffected by the presence of 1 mM hydrogen peroxide; likewise, hydrogen peroxide was not consumed by DEA/NO or intermediates of the DEA/NO decomposition reaction as measured by the production of $I_3^-$ (Hochanadel, *J. Phys. Chem.*, 56, 587–594 (1952)).

FIG. 1A is a graph of log of surviving fraction versus time (min), wherein the lines represent the exposure of cells to hypoxanthine/xanthine oxidase in the absence of a nitric-oxide releasing compound (control, O), in the presence of 0.1 mM (▲) and 1 mM (●) DEA/NO, and in the presence of 1 mM SPER/NO (■). FIG. 1A shows that exposure of V79 cells for various time intervals to HX/XO in the absence of a nitric oxide-releasing compound resulted in cell killing. Although 0.1 mM DEA/NO provided marginal protection against HX/XO generated superoxide radicals, 1 mM DEA/NO significantly protected against cell killing resulting from superoxides generated from hypoxanthine/xanthine oxidase. Accordingly, these results clearly show that hydrogen peroxide-mediated cytotoxicity can be prevented by the presence of an NO-generating compound. SPER/NO (1 mM), which releases NO 40 times slower than DEA/NO, also protected V79 cells against HX/XO induced cytotoxicity but to a lesser extent than DEA/NO. Given that the amount of NO released from SPER/NO is less than that released from DEA/NO, this further suggests that NO released from these complexes is responsible for the protection.

Another possible toxic agent in mammalian cells is peroxynitrite anion (OONO$^-$), which would be expected to form in the presence of $O_2^-$ that is generated from XO and NO (Beckman, *J. Dev. Physiol.*, 15, 53–59 (1991); Zhu et al., *Arch. Biochem. Biophys.*, 298, 452–457 (1992); Ischiropoulos et al., *Arch. Biochem. Biophys.*, 298, 431–437 (1992); and Beckman et al. (1990), supra). The reaction rate constant for NO and $O_2$ is reported to be $5.6 \times 10^7$ $M^{-1}S^{-1}$, with the product being the potent oxidant (OONO$^-$) (Saran et al., *Free Radic. Res. Commun.*, 10, 221–226 (1990)). This anion has been speculated to play a critical role in potentiating the toxic effects of NO, although OONO$^-$ is rapidly converted at physiological pH to nitrate. The quenching of $O_2^-$ reduction of ferricytochrome c by DEA/NO can be explained by the scavenging of the $O_2^-$ by NO to form peroxynitrite anion. However, any peroxynitrite anion which might be formed under the above conditions does not induce cytotoxicity as shown in FIG. 1A.

DEA/NO (1 mM) alone and its breakdown products diethylamine (1 mM) and nitrite (1 mM) preincubated with HX/XO did not inhibit the activity of XO as measured by the production of superoxide (cytochrome c reduction) or uric acid production.

FIG. 1B is a graph of log of surviving fraction versus time (min), wherein the lines represent the exposure of cells to hydrogen peroxide in the absence (control, O) and presence of the DEA/NO breakdown products diethylamine (■) and nitrite (+). FIG. 1B shows that the decomposition products of DEA/NO did not protect cells from hydrogen peroxide or HX/XO-induced cytotoxicity.

Monitoring of UV absorption changes at 305 nm also indicated that uric acid production was not inhibited by the presence of DEA/NO. Accordingly, substrate turnover is not inhibited either reversibly or irreversibly. The presence of DEA/NO, however, inhibited the SOD sensitive ferricytochrome c reduction. This suggests that either reduction of oxygen to form superoxide was inhibited or NO scavenged the HX/XO-generated superoxide to form peroxynitrite anion, which was then rapidly converted to nitrate.

Figure 2A:
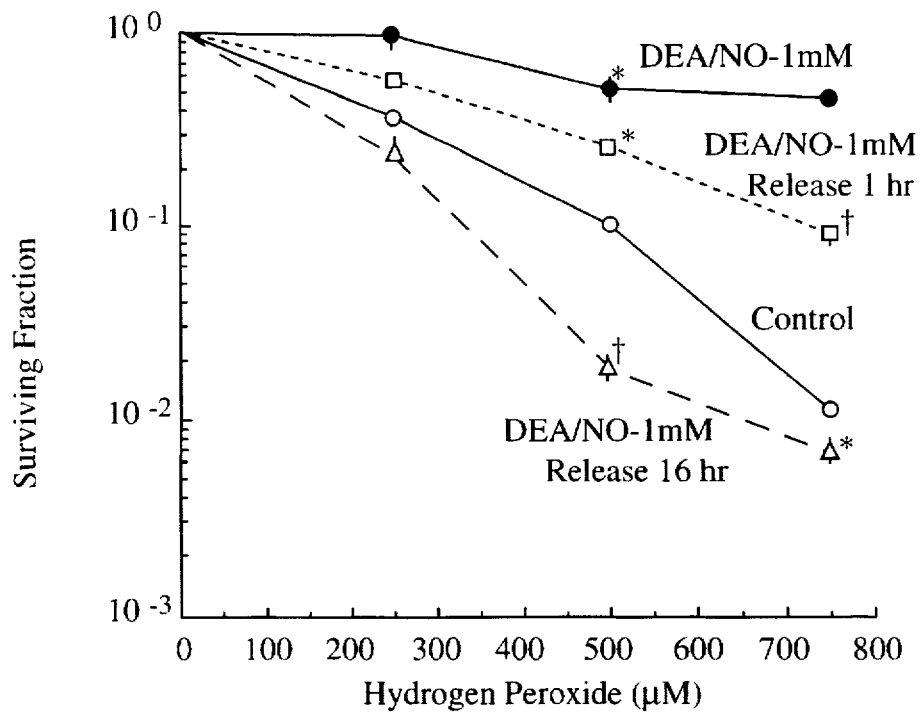
FIG. 2A is a graph of log of surviving fraction versus hydrogen peroxide concentration ($\mu$M) for cells exposed to hydrogen peroxide for 1 hr in the presence and absence of a nitric oxide-releasing compound.

FIG. 2A is a graph of log of surviving fraction versus hydrogen peroxide concentration (µM) for a 1 hr exposure, wherein the lines represent control (O), 1 mM DEA/NO (●), 1 mM DEA/NO with 1 hr release (□), and 1 mM DEA/NO with 16 hr release (▲). FIG. 2A shows that 1 mM DEA/NO provided nearly complete protection against hydrogen peroxide cytotoxicity. V79 cells exposed to a solution of 1 mM DEA/NO allowed to release NO for 1 hr prior to addition of hydrogen peroxide exhibited only modest protection and was not as effective as DEA/NO added just prior to hydrogen peroxide addition. However, 1 mM DEA/NO incubated for 16 hr in medium prior to addition of hydrogen peroxide enhanced the cytotoxicity of hydrogen peroxide. Similarly, cells treated for one hour with hydrogen peroxide followed by a 1 hr treatment with 1 mM DEA/NO did not treat oxygen free radical mediated tissue damage.

Figure 2B:
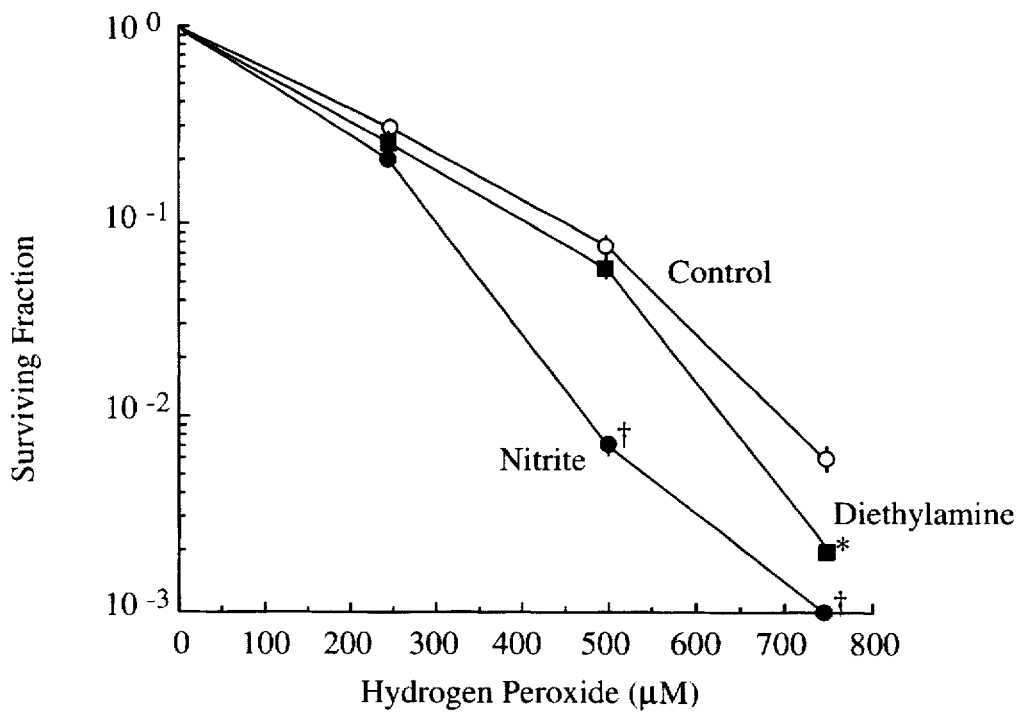
FIG. 2B is a graph of log of surviving fraction versus hydrogen peroxide concentration ($\mu$M) for cells in the presence and absence of the breakdown products of a nitric oxide-releasing compound.

FIG. 2B is a graph of log of surviving fraction versus hydrogen peroxide concentration (µM), wherein the lines represent control (O), diethylamine (■), and nitrite (●). FIG. 2B shows that diethylamine (1 mM) had no effect on hydrogen peroxide cytotoxicity, while nitrite (1 mM) potentiated hydrogen peroxide cytotoxicity. In vivo, however, very little nitrite is generated and it is rapidly excreted form the body.

Chemical controls demonstrated that the rate of formation of NO due to the decomposition of DEA/NO was not altered by the presence of hydrogen peroxide. Conversely, hydrogen peroxide was not consumed in the presence of DEA/NO. These results show that the decomposition of DEA/NO did not consume hydrogen peroxide or HX/XO nor affect XO substrate turnover and that the NO-generating compounds are mediating the cell protection and must be present during hydrogen peroxide exposure in order to be protective.

EXAMPLE 2

This example describes the protection against peroxide-mediated damage of neuronal function in ventral mesencephalic cells by nitric-oxide containing compounds that spontaneously release nitric oxide under physiological conditions without requiring the presence of oxygen.

The ventral tegmental mesencephalon was dissected from 14 day old embryos (precisely timed pregnant Sprague Dawley rats; Zivic-Miller, Allison Park, Pa.) under sterile conditions and mechanically dissociated into complete culture medium. The culture medium consisted of a 1:1 mixture of modified minimum essential medium and nutrient mixture F-12 supplemented with 6 mg/ml D-gluose, 2 mM glutamine, 0.5 U/ml penicillin G, 0.5 mg/ml streptomycin (all from Gibco, Grand Island, N.Y.) and 15% equine serum (Hyclone, Logan, Utah). Cells were plated into multiwell plates that were previously coated with poly-D-lysine (15 µg/ml) and laminin (10 µg/ml) at a density of 40,000 cells/cm$^2$ (Costar). The cells were maintained for 5–7 days at 37° C. in an atmosphere of 95% air and 5% $CO_2$ saturated with $H_2O$. On the fifth day of culture 1 µM cytosine-β-D-arabinofuranoside was added to inhibit glial cell growth.

Uptake of dopanine by dopaminergic neurons was assayed as follows. The cells in each well were washed three times with 1 ml PBS containing 6 mg/ml glucose and thereafter Dulbecco's modified essential medium (Quality Biological, Inc., Farmingham, Mass.) containing 6 mg/ml D-glucose, 50 µM ascorbic acid, and 5×10$^{-8}$M [$^3$H] dopamine (NEN, Boston, Mass.; specific activity of 45 µCi/mmol) was added and incubated for 15 min at 37° C. [$^3$H]dopamine uptake was stopped by aspirating the incubation solution and washing the cells three times with ice-cold PBS containing 6 mg/ml D-glucose. The cells were removed by washing the wells with an equal volume of 0.2N NaOH and 0.2N HCl containing 0.02% Triton X-100. The residual intracellular radioactivity in the cells was determined by scintillation spectroscopy.

Accordingly, ventral mesencephalic cell cultures were exposed to 100 µM $H_2O_2$ for 1 hr in the presence and absence of 100 µM DEA/NO and evaluated for their ability to take up dopamine.

Figure 3:
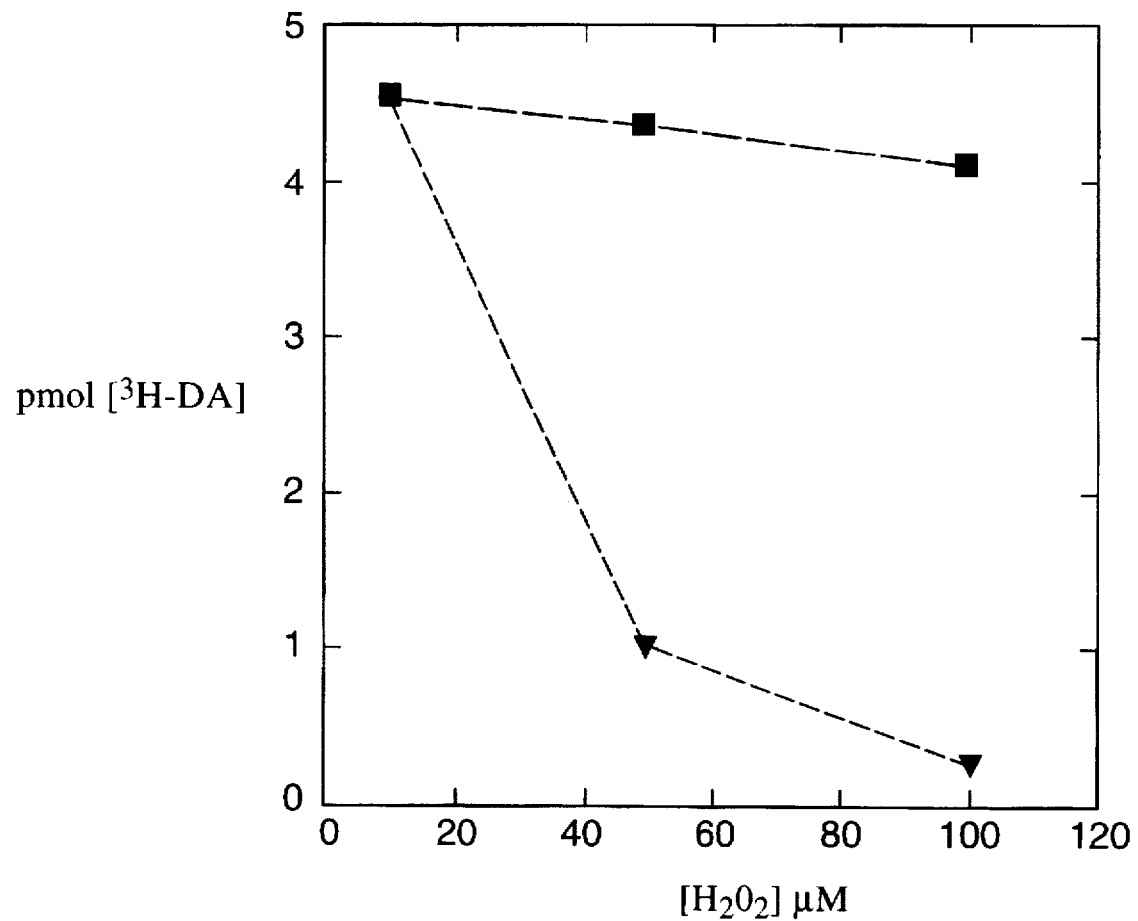
FIG. 3 is a graph of $^3$H-dopamine concentration (pmol) versus hydrogen peroxide concentration ($\mu$M) for ventral mesencephalic cells in the presence and absence of a nitric oxide-releasing compound.

FIG. 3 is a graph of $^3$H-dopamine concentration (pmol [$^3$H-DA]) versus $H_2O_2$ concentration ([$H_2O_2$] µM), wherein lines represent dopamine uptake by ventral mesencephalic cell cultures in the presence (■) and absence (▲) of DEA/NO. FIG. 3 shows that hydrogen peroxide significantly reduced the ability of the cells to take up dopamine in the absence of DEA/NO, whereas cells exposed to hydrogen peroxide in the presence of DEA/NO retained nearly 100% of their function.

In a separate study, cells were cultured for 7 days and then exposed to 50 or 100 µM hydrogen peroxide for 60 min or to 0.04 units/ml HX/XO for 5 or 10 min in the absence or presence of 100 µM DEA/NO. The cells were washed with PBS containing 6 g/l D-glucose, culture medium was added, and the cells were incubated for 18 hr. The ability of the cells (6 wells of 450,000 cells/well per group) to take up $^3$[H]-dopamine was measured. These cells were exposed to ten times less hydrogen peroxide or HX/XO than the V79 cells described above. The results are shown in Table I.

TABLE I

| Addition to Incubation Medium | Time of Exposure | [$^3$H] Dopamine Uptake (pmol/well/15 min) | |
|---|---|---|---|
| | | Control | 100 µM DEA/NO |
| None | | 2.9 ± 0.20 | 2.7 ± 0.11 |
| 50 µM $H_2O_2$ | 60 min | 0.63 ± 0.15* | 2.8 ± 0.11 |
| 100 µM $H_2O_2$ | 60 min | 0.15 ± 0.014* | 2.6 ± 0.22 |
| 0.04 U/ml HX/XO | 5 min | 1.1 ± 0.21* | 2.6 ± 0.15 |
| 0.04 U/ml HX/XO | 10 min | 0.36 ± 0.21* | 2.3 ± 0.10 |

* $p < 0.01$ when compared with non-treated group (Student's t-Test)

As shown in Table I, when 100 µM DEA/NO was added together with the hydrogen peroxide or HX/XO, complete protection was observed. Since radiolabeled dopamine uptake can be used as a measure of neurite viability, it can be inferred that NO protects neurons from damage induced by reactive oxygen species.

When cells were exposed to hydrogen peroxide for 1 hr, varicosities formed in the neurites and somas swelled. Exposure to HX/XO for as short as 5 min elicited similar morphological changes in mesencephalic neurons. In contrast, cells exposed to 100 µM DEA/NO for 1 hr failed to cause morphological changes, i.e., DEA/NO-treated cells resembled non-treated cells. Cells exposed to hydrogen peroxide or HX/XO in the presence of 100 µM DEA/NO did not demonstrate abnormalities in the neurites and somas.

EXAMPLE 3

This example describes the initiation of reperfusion-induced leukocyte adhesion and microvascular permeability by diminished nitric oxide release.

Male Sprague-Dawley rats weighing 200–250 g apiece were maintained on a purified laboratory diet and fasted for 24 hours prior to each experiment. The animals were initially anesthetized with pentobarbital (65 mg/kg body weight) and then a tracheotomy was performed to facilitate breathing during subsequent experimentation. The right carotid artery was cannulated and system arterial pressure was measured with a Statham P23A pressure transducer (Oxnard, Calif.) connected to the carotid artery cannula. Systemic blood pressure and heart rate were continuously recorder with a Grass physiologic recorded (Grass Instruments). The left jugular vein and superior mesenteric artery were also cannulated for drug administration.

Rats were placed in a supine position on an adjustable plexiglass microscope stage and the mesentery was prepared for microscopic observation as described previously (Asako et al., *Gastroenterology*, 103, 146–152 (1992); Kurose et al., *Circ. Res.*, in press (1993)). Briefly, the mesentery was draped over a non-fluorescent coverslip that allowed for observation of a 2 cm$^2$ segment of tissue. The exposed bowel wall was covered with Saran Wrap (Dow Chemical Co.) and the mesentery was superfused with bicarbonate-buffered saline (pH 7.4, 37° C.) that was bubbled with a mixture of 5% $CO_2$ and 90% $N_2$.

An inverted microscope (TMD-25, Diaphoto, Nikon, Tokyo, Japan) with a 40x objective lens (Fluor, Nikon) was used to observe the mesenteric microcirculation. The mesentery was transilluminated with a 12 V-100 W direct current-stabilized light source. A video camera (VK-C150, Hitachi, Ibaragi, Japan) mounted on the microscope projected the image onto a color monitor (PVM-2030, Sony, Tokyo, Japan) and the images were recorded using a videocassette record (NV8950, Panasonic, Tokyo, Japan). A video time-date generator (WJ810, Panasonic) projected the time, date and stopwatch function onto the monitor.

Single unbranched venules with diameters ranging between 25 and 35 µm and length greater than 150 µm were selected for study. Venular diameter (DV) was measured either on- or off-line using a video caliper (Microcirculation Research Institute, Texas A&M University, College Station, Tex.). Red blood cell centerline velocity (VRBC) was measured in venules using an optical Dopper velocimeter (Microcirculation Research Institute, Texas A&M University, College Station, Tex.). The velocimeter was calibrated against a rotating glass disk coated with red blood cells. Venular blood flow was calculated from the product of mean red blood cell velocity ($V_{mean}$=centerline velocity/1.6; Davis, Microvasc. Res., 34, 223–230 (1987)) and microvascular cross-sectional area, assuming cylindrical geometry. Wall shear rate ($\gamma$) was calculated based on the Newtonian definition $\gamma=8(V_{mean}/D)$.

The number of adherent leukocytes was determined off-line during playback of videotape images. A leukocyte was considered to be adherent to venular endothelium if it remained stationary for a period equal to or greater than 30 seconds (Granger et al., Am. J. Physiol., 257, G683–G688 (1989)). Adherent cells were expressed as the number per 100 µm length of venule. The number of emigrated leukocytes was also determined off-line during playback of videotape images. Any interstitial leukocytes present in the mesentery at the onset of the experiment were subtracted from the total number of leukocytes that accumulated during the course of the experiment. Leukocyte emigration was expressed as the number per field of view surrounding the venule. Platelet-leukocyte aggregates, which were visible within postcapillary venules, were quantitated and expressed as the number of aggregates crossing a fixed point within the venule over a 5 min period. Mast cells in the microvascular beds of the rat mesenteries were visualized by using 0.1% toluidine blue. The number of normal and degranulated mast cells was determined and the percentage of degranulated mast cells was calculated.

Albumin leakage across mesenteric venules was quantified by administering 50 mg/kg of FITC-labeled bovine albumin (Sigma Chemical Co., St. Louis, Mo.) intravenously 15 min before each experiment (Kurose et al., supra). Fluorescence intensity (excitation wavelength of 420–490 nm; emission wavelength of 520 nm) was detected using a silicon intensified target camera (C-2400-08, Hamamatsu Photonics, Skizuoka, Japan). The fluorescence intensity of FITC-albumin within 3 segments of the venule under study (Iv) and in 3 contiguous areas of perivenular interstitium (Ii) area were measured at various times after administration of FITC-albumin using a computer-assisted digital imaging processor (Macintosh, Apple Co.). An index of vascular albumin leakage was determined from the ratio of Ii:Iv at specific times during the reperfusion phase.

After all parameters measured on-line were in a steady state, images from the mesenteric preparation were recorded on videotape for 10 min. Immediately thereafter, the superior mesenteric artery was ligated with a snare created from polyethylene tubing. The mesentery was made ischemic for zero (sham ischemia) or 20 min. After the ischemic period, the ligation was gently removed. In some experiments, either sodium nitroprusside (SNP, 100 µM, Sigma Chemical), spermine-NO (SpNO, 100 µM), SIN-1 (100 µM), spermine (SP, 100 µM, Sigma Chemical), or NG-nitro-L-arginine methyl ester (L-NAME, 100 µM, Sigma Chemical) was added to the superfusate and the same protocol was employed. Spermine-NO and SIN-1, which are NO donors, were obtained from the National Institutes of Health, Bethesda, Md.

Plasma levels of nitrite and nitrate were determined by a modification of the method of Green et al. (Anal. Biochem., 126, 131–138 (1982)) and Yamada et al. (Gastroenterology, 104, 759–771 (1993)). Briefly, 400 µl of distilled water were added to 100 µl of heparinized plasma. Protein was precipitated by the addition of 25 µl 30% $ZnSO_4$. Five minutes after the addition of $ZnSO_4$, the precipitant was removed by centrifugation. Five hundred microliters of the supernatant were added to 25 µl of E. coli-derived nitrate reductase, 20 µl of 2.5M HEPES, and 50 µl of 3M $NH_4$ formate (pH 7.4), and incubated with the reductase for 1 hr at 37° C. to reduce nitrate to nitrite (Bartholomew, Food Chem. Toxicol., 22, 541–543 (1984)). Nitrite in the incubated sample was quantified by the method of Stuehr et al. (Sartor et al., Gastroenterology, 89, 587–595 (1985)) using the Griess reagent (1% sulfanilamide/0.1% naphthylethylenediamine dihydrochloride/2.5% $H_3PO_4$). Nitrite concentrations were calculated from a standard curve using sodium nitrite (Sigma Chemical) as the standard. The data were analyzed using standard statistical analysis, i.e., one-way analysis of variance and Scheffe's (post-hoc) test. All values were reported as mean ± standard error from 6 rats and statistical significance was set at $p<0.05$.

In untreated (control) rats, the RBC velocity and wall shear rate in mesenteric venules were 3.12±0.18 mm/sec and 535±6 $\sec^{-1}$, respectively, under control conditions. During occlusion of the superior mesenteric artery (SMA), blood flow ceased within mesenteric venules. Ischemic periods up to 20 min duration were associated with significant and sustained reperfusion, i.e., RBC velocity (1.94±0.13 mm/sec) and wall shear rate (328±16 $\sec^{-1}$) were restored toward normal values following release of the SMA occlusion. Longer durations of ischemia (>30 min) were not associated with a consistent reperfusion response with flow rarely occurring to a significant extent after release of the SMA occlusion. Consequently, measurements of leukocyte-endothelial cell adhesion and albumin leakage were obtained only in mesenteric venules exposed to 20 min ischemia. NO donors, i.e., SNP, SpNO, and SIN-1, but not SP or L-NAME, reversed the decreases in RBC velocity and wall shear rate after the reperfusion. These data are summarized in Table II.

TABLE II

Venular diameter, RBC velocity and wall shear rate at 30 min after reperfusion

| Treatment | Diameter (µm) | RBC velocity (mm/sec) | Wall Shear Rate (l/sec) |
|---|---|---|---|
| Control | 29.2 ± 1.8 | 3.12 ± 0.18 | 535 ± 6 |
| I/R | 29.6 ± 1.4 | 1.94 ± 0.13* | 328 ± 16* |
| SNP | 29.4 ± 1.1 | 2.68 ± 0.16† | 456 ± 22† |
| SIN1 | 29.0 ± 1.1 | 2.64 ± 0.23 | 457 ± 38† |
| SPNO | 31.8 ± 2.1 | 3.06 ± 0.28† | 480 ± 27† |
| SP | 29.8 ± 1.4 | 2.32 ± 0.19 | 391 ± 28 |
| L-NAME | 29.2 ± 1.5 | 1.84 ± 0.09 | 316 ± 10 |

*p < 0.05 vs. Control group
†p < 0.05 vs. I/R untreated group

Figure 4A:
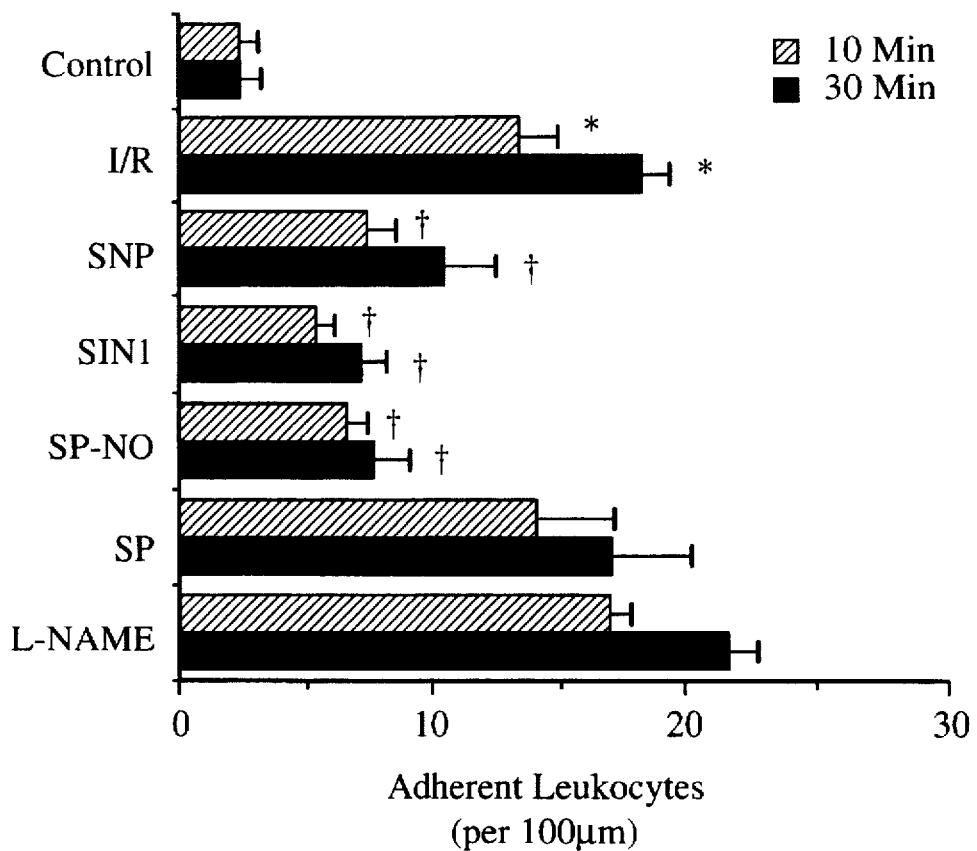
FIGS. 4A–C are bar graphs of NO donors and NO synthesis inhibitors versus number of adherent leukocytes per 100 $\mu$m, emigrated leukocytes per field, and % albumin leakage, respectively, for 20 min ischemia and 30 min reperfusion with data shown for 10 min and 30 min reperfusion.
Figure 4B:
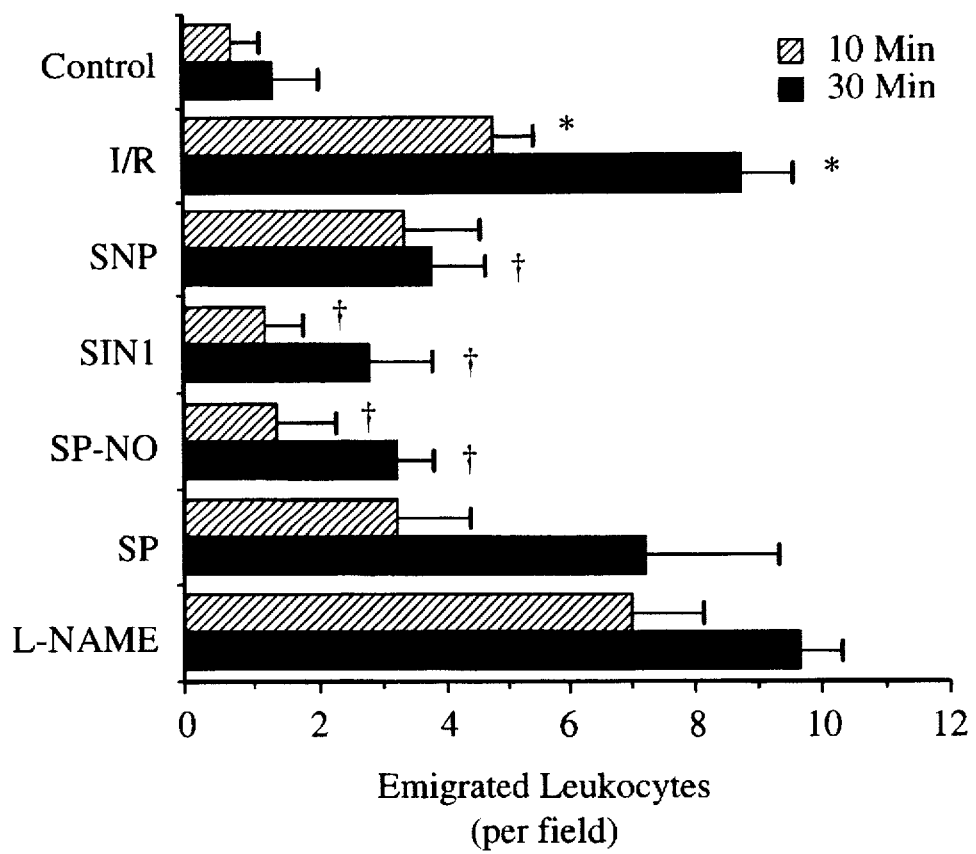
Figure 4C:
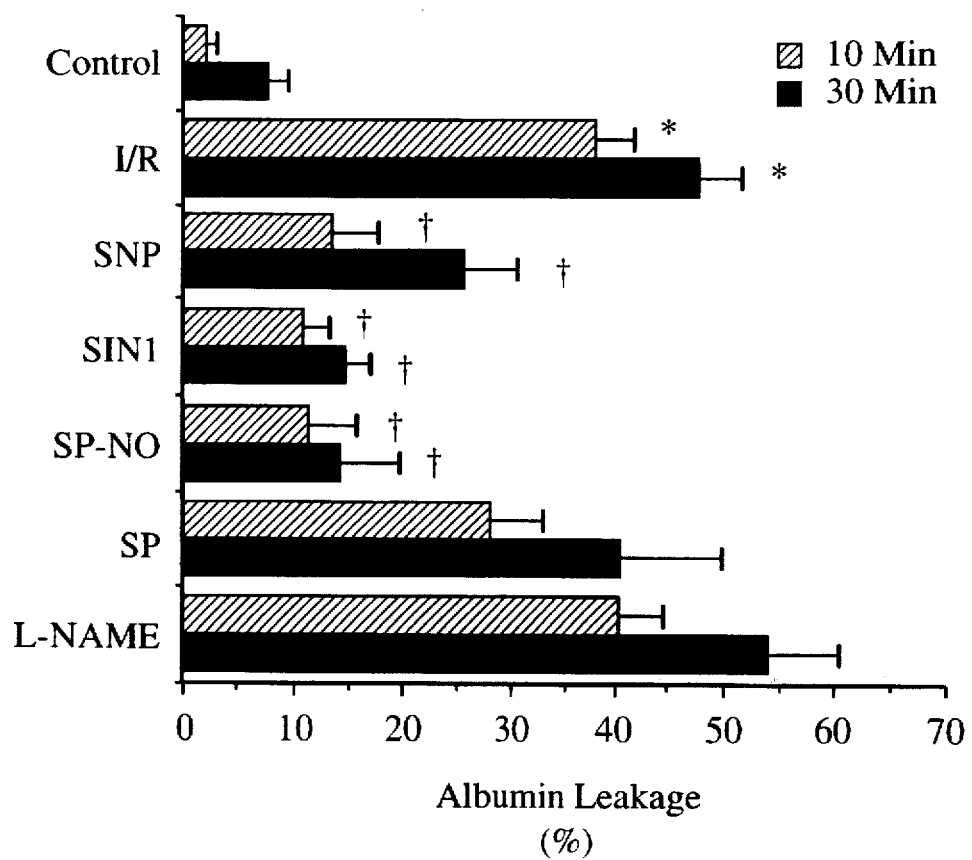

FIGS. 4A–C are bar graphs of NO donors and NO synthesis inhibitor versus number of adherent leukocytes per 100 µm, emigrated leukocytes per field, and % albumin leakage, respectively, for 20 min ischemia and 30 min reperfusion with data shown for 10 min and 30 min reperfusion. Error bars represent standard deviations from the mean. The number of adherent and emigrated leukocytes were significantly elevated at 10 min after reperfusion and increased progressively thereafter. In animals subjected to 20 min of sham ischemia and 30 min of reperfusion, leukocyte adherence was 2.6±0.8 per 100 μm with 1.4±0.7 emigrated leukocytes per field and an albumin leakage index of 8.3±1.6%. Corresponding values obtained in mesenteric preparations exposed to 20 min of ischemia and 30 min reperfusion were 18.4±1.0 per 100 μm, 8.8±0.8 per field, and 48.1±4.0%, respectively. However, no significant changes in leukocyte adherence were noted in animals receiving either SP- or L-NAME (see FIG. 4A). A similar pattern of effectiveness in reducing leukocyte emigration (FIG. 4B) was observed with the different NO donors, i.e., SNP, SPNO, and SIN-1 reduced the number of emigrated leukocytes by 29–57%, 64–71%, and 68–75%, while SP- and L-NAME had no effect. FIG. 4C illustrates that the large increase in albumin leakage induced by ischemia reperfusion was significantly attenuated by SNP (46–63%), SpNO (70%), and SIN-1 (60–71%) at both 10 min and 30 min after reperfusion. SP- and L-NAME had no effect on ischemia reperfusion induced albumin leakage.

Figure 5A:
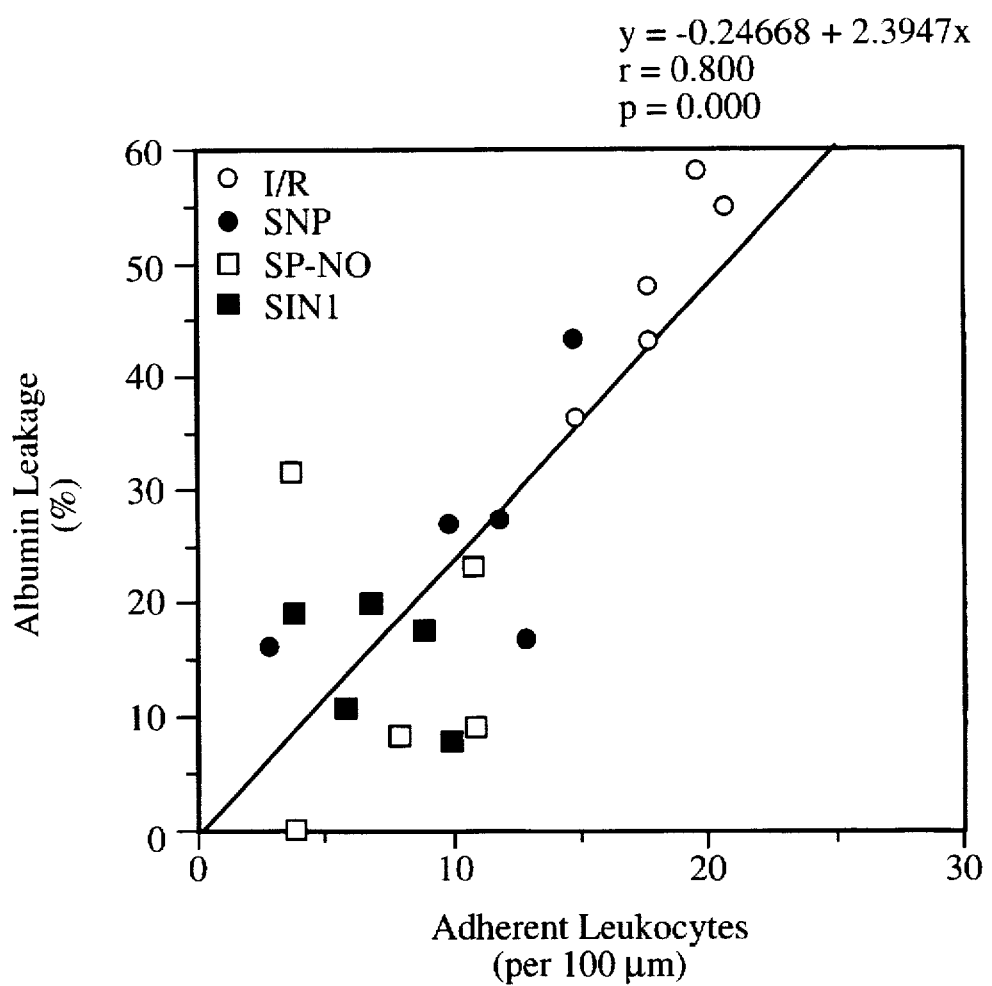
FIGS. 5A and B are graphs of % albumin leakage versus adherent leukocytes per 100 $\mu$m and emigrated leukocytes per field, respectively.
Figure 5B:
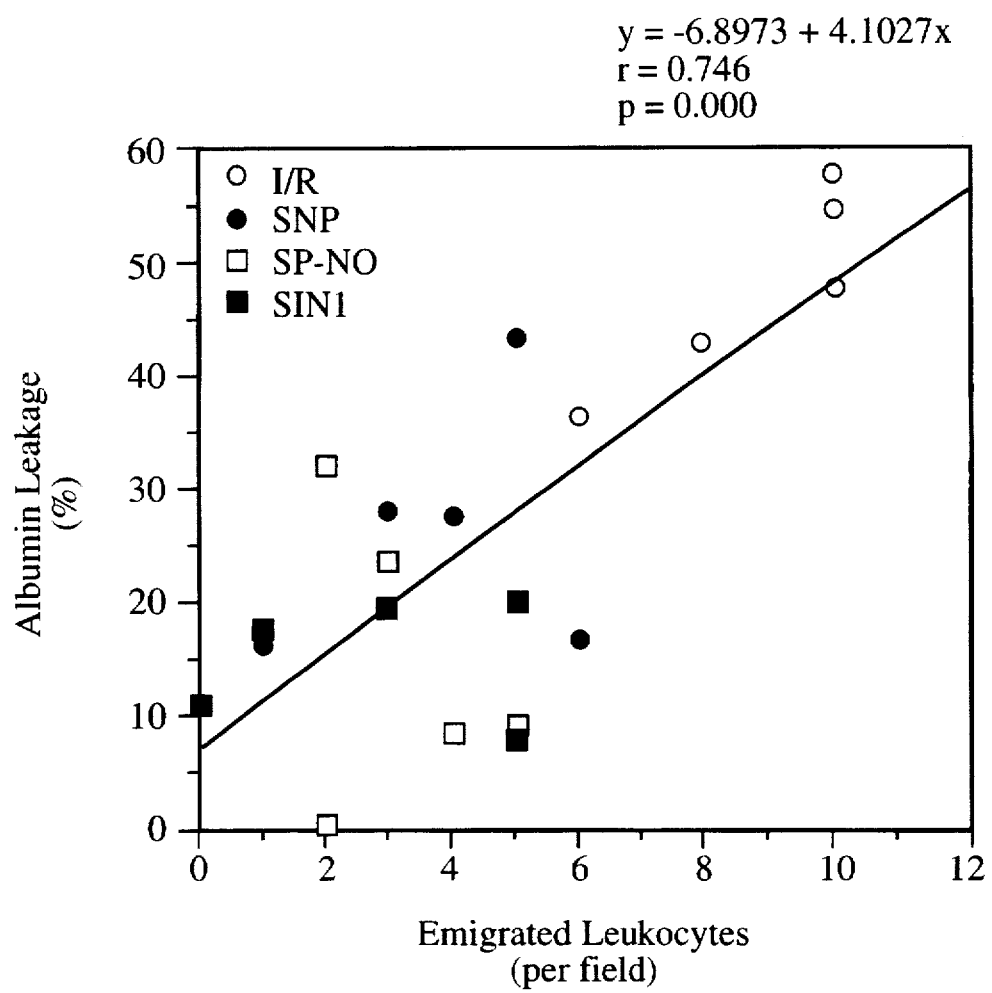

FIGS. 5A and B are graphs of % albumin leakage versus adherent leukocytes per 100 μm and emigrated leukocytes per field, respectively. FIG. 5 illustrates the dependence of ischemia reperfusion-induced albumin leakage in single venules on the number of adherent (FIG. 5A) and emigrated (FIG. 5B) leukocytes. All values were derived from the 30 min values presented in FIG. 4. Albumin leakage was highly correlated with both leukocyte adherence ($r=0.800$, $p<0.05$) and leukocyte emigration ($r=0.746$, $p<0.05$). Albumin leakage was greater in regions of the venule which exhibited a high level of leukocyte adherence/emigration than in regions exhibiting little or no adherence/emigration.

Figure 6:
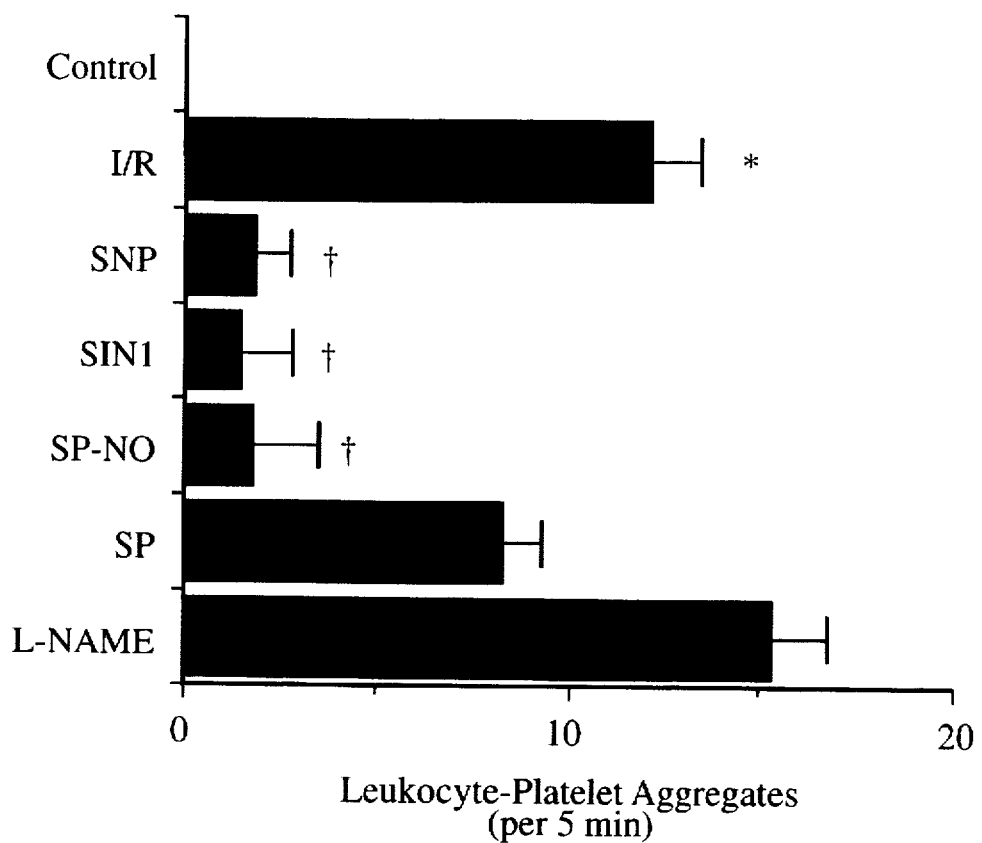
FIG. 6 is a bar graph of compounds versus leukocyte-platelet aggregates per 5 min.

FIG. 6 is a bar graph of compounds versus leukocyte-platelet aggregates per 5 min. Error bars represent standard deviations from the mean. FIG. 6 summarizes the effects of NO donors on ischemia reperfusion induced formation of platelet-leukocyte aggregates. Although aggregates were never observed during control conditions, 12.2±1.4 aggregates per 5 min were observed in venules exposed to 20 min of ischemia and 30 min of reperfusion. Aggregate formation was reduced in animals treated with either SNP, SpNO or SIN-1, but not with SP- or L-NAME.

Figure 7:
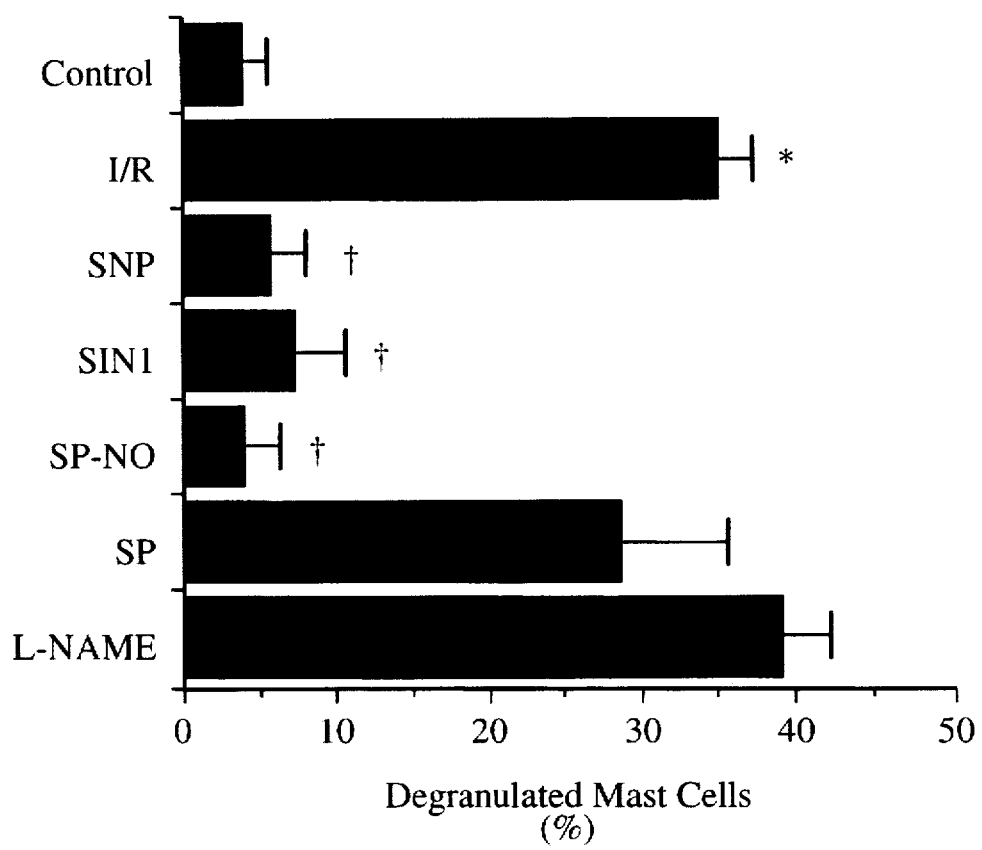
FIG. 7 is a bar graph of compounds versus % degranulated mast cells.

FIG. 7 is a bar graph of compounds versus % degranulated mast cells. Error bars represent standard deviations from the mean. FIG. 7 summarizes the effects of NO donors on ischemia reperfusion induced degranulation of microvascular mast cells. Degranulated mast cells were less than 5% of the total mast cells observed along postcapillary venules of control rats 30 minutes after reperfusion. Degranulated mast cells increased to approximately 35% after 20 min ischemia followed by 30 min reperfusion. SNP, SpNO, and SIN-1 significantly inhibited ischemia-reperfusion induced degranulation of microvascular mast cells, while SP- or L-NAME alone had no effect.

Figure 8:
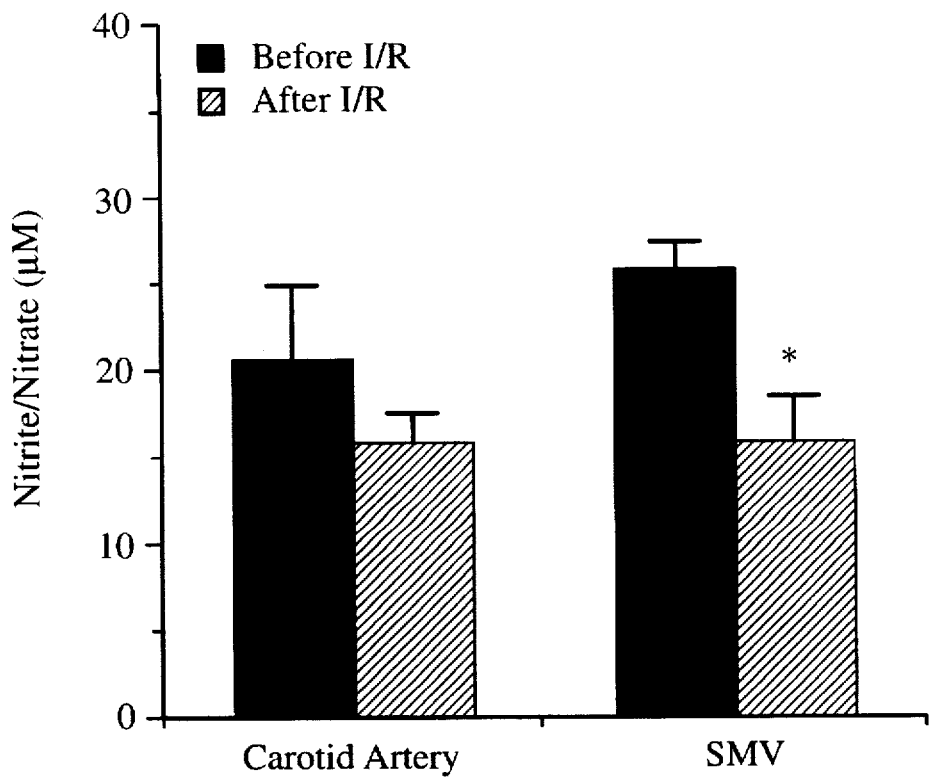
FIG. 8 is a bar graph of nitrite/nitrate concentration ($\mu$M) versus carotid artery and superior mesenteric vein (SMV) before and after ischemia reperfusion (I/R).

FIG. 8 is a bar graph of nitrite/nitrate concentration (μpM) versus carotid artery and superior mesenteric vein (SMV) before and after ischemia reperfusion (I/R). Error bars represent standard deviations from the mean. Nitrite and nitrate concentration in the superior mesenteric vein was 25.82±1.76 μmole. After ischemia reperfusion, the nitrite and nitrate concentration decreased to 15.67±2.73 μmole. Nitrite and nitrate concentration in the carotid artery, however, showed no significant alteration after ischemia reperfusion (before: 20.34±4.21; after: 15.51±1.79).

EXAMPLE 4

This example demonstrates the effects of nitric oxide-containing compounds on the mucosa and microvasculature in cats which have undergone transplants of the small intestine during hypothermic ischemia.

Donor cats were fasted for 18–24 hours and were anesthetized by intramuscular injection of approximately 75 mg ketamine hydrochloride and 0.5 mg acepromazine maleate followed by intravenous anesthesia with pentobarbital sodium through a right jugular vein cannula. The cats were mechanically ventilated with a Harvard respirator after completion of tracheotomies.

A midline laparotomy was performed, the colon removed, and a 10–20 g segment of distal ileum was isolated. Inflow and outflow rubber cannulas were put in place and secured. The remainder of the small intestine was resected and removed from the operative field. The cats were then administered 10,000 units of heparin intravenously. A large lymphatic vessel in the mesenteric pedicle was cannulated and secured with 4–0silk ligatures.

The lumen of the small intestine specimen was flushed with 200–300 ml of cold Ringer's lactate at 50 cm $H_2O$. Both the superior mesenteric artery and vein were cannulated and the artery was flushed with 100 ml of cold Ringer's lactate at 35 cm $H_2O$.

The proximal mesenteric pedicle was ligated and the harvested segment was removed for placement on a plexiglass platform and moistened with cold Ringer's lactate. The harvested small intestine was placed in a humidified, airtight plexiglass chamber and refrigerated at 4° C. for 6 hours.

The recipient operation was identical in procedure to the donor model up to the laparotomy. At this point, both renal arteries were ligated with 4–0 silk ligatures to prevent renal excretion of $^{51}$Cr-EDTA (New England Nuclear, Boston, Mass.). $^{51}$Cr-EDTA is widely used to examine subtle changes in the intestinal mucosa. EDTA is a small molecule with a molecular weight of 359 and its chromium chelate will rapidly equilibrate with the extracellular compartment after intravenous administration. The rate-limiting barrier for blood-to-lumen movement of this molecule is the epithelial cell monolayer of the intestinal mucosa, which is also independent of changes in the endothelial cell layer of the microvasculature (Kubes (1992), supra; Crissinger et al., *J. Intern. Med. Suppl.*, 1, 145–154 (1990)).

Heparin (10,000 units) was injected intravenously and the vena cava and aorta were cannulated with silastic cannulas. The laparotomy incision was closed with the inferior aspect open to allow placement of a flow probe/Statham 23 A transducer to form the arterial circuit. The venous circuit also included a pressure transducer. A Grass physiological recorder was used upon reperfusion of the intestinal segment to monitor arterial, venous, and capillary pressure. Capillary pressure was measured using a previously described venous occlusion technique (Granger et al., *Am. J. Physiol.*, 244, G341–344 (1983)). The donor intestinal segment was covered with clear plastic wrap to minimize evaporative water loss while the temperature was maintained at 38°–40° C. with an infrared heat lamp and thermometer.

On reperfusion of the intestinal graft, the lumen was perfused with warm (38° C.) Ringer's lactate at a rate of 1.0 ml/min, while the effluent was collected at 5 min intervals for 120 minutes. Five hundred μCi $^{51}$Cr-EDTA was injected intravenously after approximately 20–30 minutes on determination of a well-functioning graft. By allowing 30 min to elapse after injection, $^{51}$Cr-EDTA was allowed to equilibrate in the tissue. All 5 min samples of luminal perfusate were centrifuged at 3700 rpm at 4° C. for 20 min. The supernate was saved and weighed. $^{51}$Cr-EDTA activity of the supernate was measured in a LKB CompuGamma spectrometer (model 1282, LKB Instruments, Gaithersburg, Md.). The $^{51}$Cr-EDTA clearance was calculated and expressed as ml/min/100 g tissue weight according to the following formula:

$$^{51}Cr\text{-}EDTA\ clearance = \frac{\text{perfusate (cpm/ml)} \times \text{perfusion rate (ml/min)} \times 100}{\text{plasma (cpm/ml)} \times \text{tissue weight (g)}}.$$

Lymph flow and concentration were obtained every 15 min during reperfusion using the cannulated mesenteric lymph vessel. Using a 200 μl calibrated pipette, lymph flow ($J_L$) was observed. Lymph ($C_L$) and plasma ($C_p$) protein concentrations were measured with an American Optical Refractometer. Prior to vascular flushing during the harvest procedure, control values for $C_L$, $C_p$, and $J_L$ were obtained. All calculated intestinal values were normalized per 100 g tissue. Lymph protein clearance was calculated using the formula:

Lymph protein clearance=$(C_L Q_L)/C_P$.

The animals were then divided into three different groups. The first group did not receive any therapeutic intervention and was divided into one control group and one group subjected to 6 hours of hypothermic ischemia. The control group involved an intestinal specimen merely for in situ control values and did not undergo ischemia or luminal flushing with Ringer's lactate.

The second group underwent the identical procedure as the untreated 6-hr hypothermic ischemia group. However, the intestinal lumen was perfused with 0.1 mmol spermine NO in Ringer's lactate. A fresh solution of 0.1 mmol spermine NO as luminal perfusate was used every 30 minutes secondary to the short half-life of 39 minutes (Maragos et al., *J. Med. Chem.*, 34 (11), 3242–3247 (1991)). The perfusate was kept at 38° C. in a monitored warm water bath.

A subgroup of the second group involved an identical experimental procedure except 0.1 mmol spermine base (Sigma) in Ringer's lactate was used as a control to compare versus spermine NO.

The third group was identical to the 6 hr untreated hypothermic ischemia group except 0.5 mmol SIN-1 in Ringer's lactate was used as luminal perfusate every 30 minutes. The light-sensitive SIN-1 solution was kept covered with aluminum foil and maintained at 38° C. in a warm water bath.

Using conventional statistical methods, independent t-tests were performed. All statistical values were reported as means ± S.D. with p<0.05.

Figure 9:
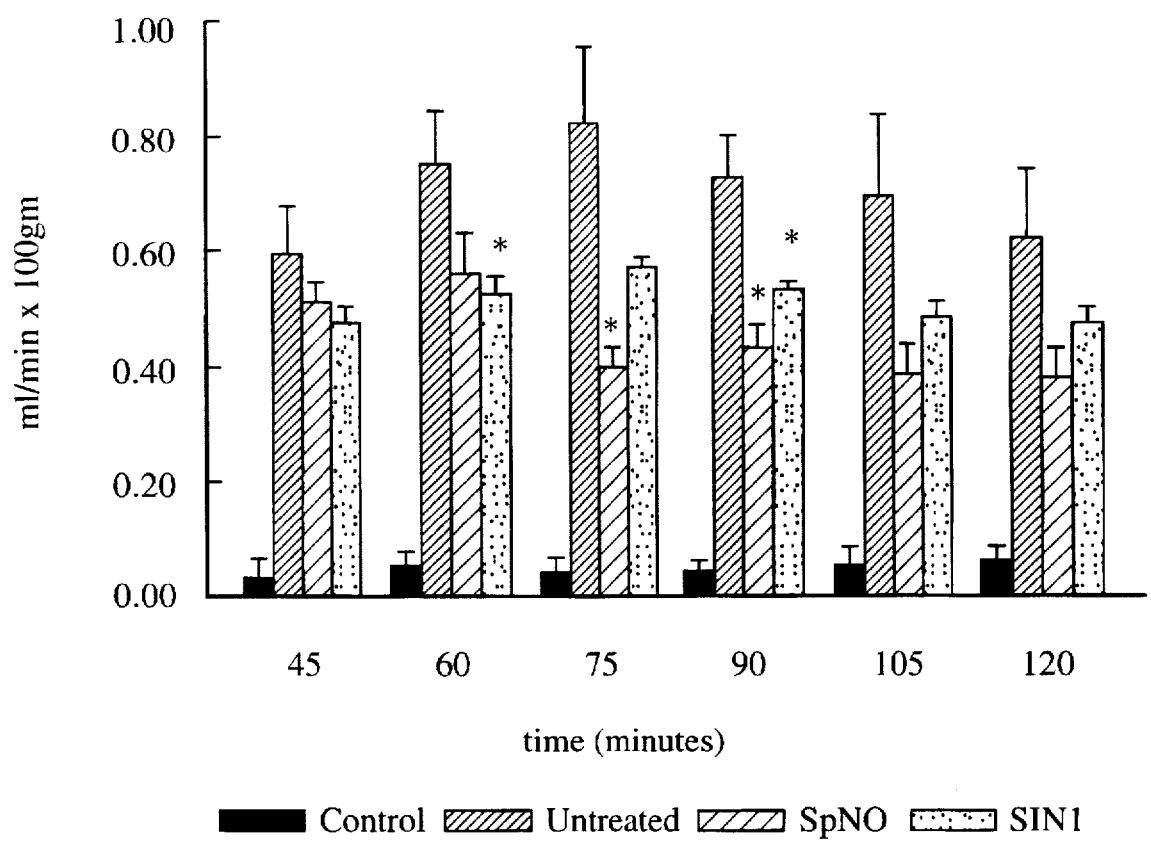
FIG. 9 is a bar graph of $^{51}$Cr-EDTA clearance (ml/min× 100 g) versus time (min) for control, untreated, SpNO-treated, and SIN-1-treated animals.

Intestinal blood to lumen $^{51}$Cr-EDTA clearance (ml/min× 100 g) was measured during 120 minutes of reperfusion. The clearance from blood to lumen is a measure of mucosal permeability. FIG. 9 is a bar graph of $^{51}$Cr-EDTA clearance (ml/min×100 g) versus time (min) which shows the $^{51}$Cr-EDTA clearance in 6-hr hypothermic ischemia test animals, including control, untreated, SpNO-treated, and SIN-1-treated, every 15 min for 120 min. Error bars represent the mean ± S.D. FIG. 9 shows that mucosal permeability decreased in those animals treated with spermine NO and SIN-1. A statistically significant decrease in $^{51}$Cr-EDTA clearance was noted at 75 and 90 min with spermine NO and at 60 and 90 min for SIN-1.

Figure 10:
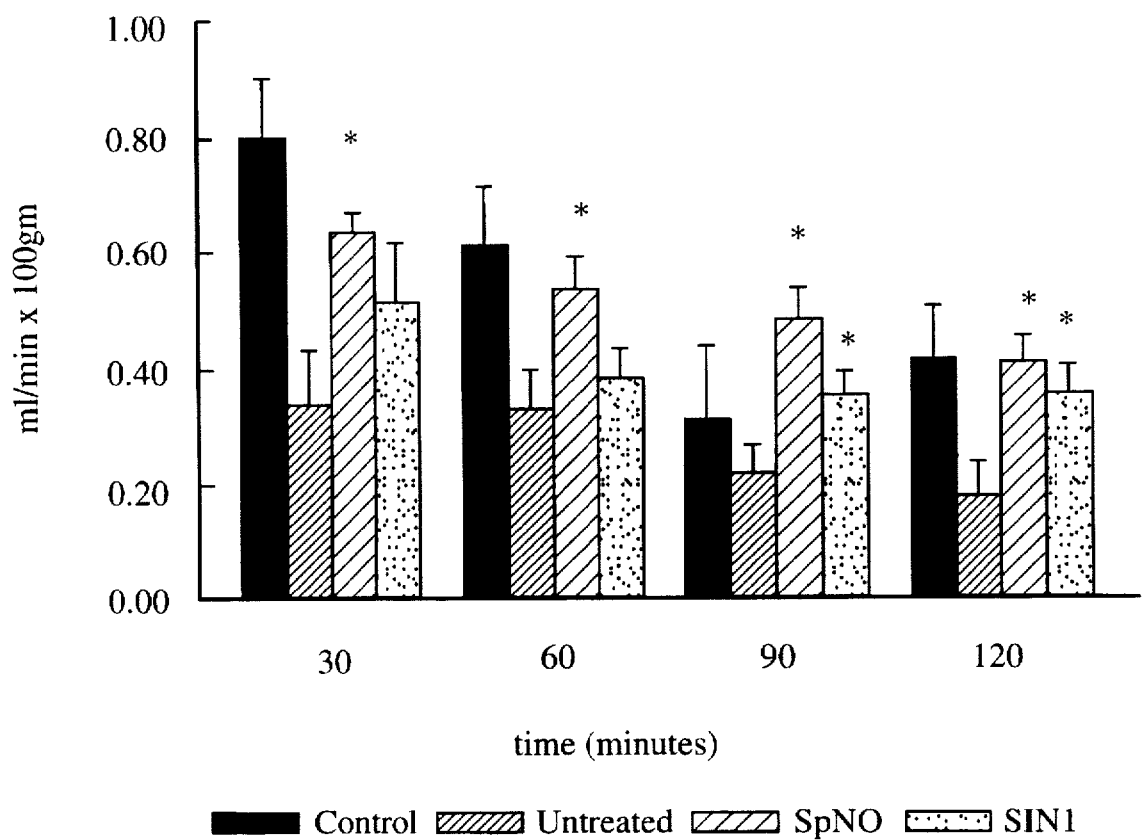
FIG. 10 is a graph of water absorption (ml/min×100 g) versus time (min) for control, untreated, SpNO-treated, and SIN-1-treated animals.

Secondary to the mucosal barrier injury, water absorption normally decreases with ischemia reperfusion. FIG. 10 is a graph of water absorption (ml/min×100 g) versus time (min) for control, untreated, SpNO, and SIN-1 treated animals. Error bars represent the mean ± S.D. FIG. 10 shows that water absorption increased significantly during 120 min of reperfusion in animals treated with spermine NO as opposed to untreated animals. SIN-1 administration significantly increased water absorption at 90 and 120 min.

Figure 11:
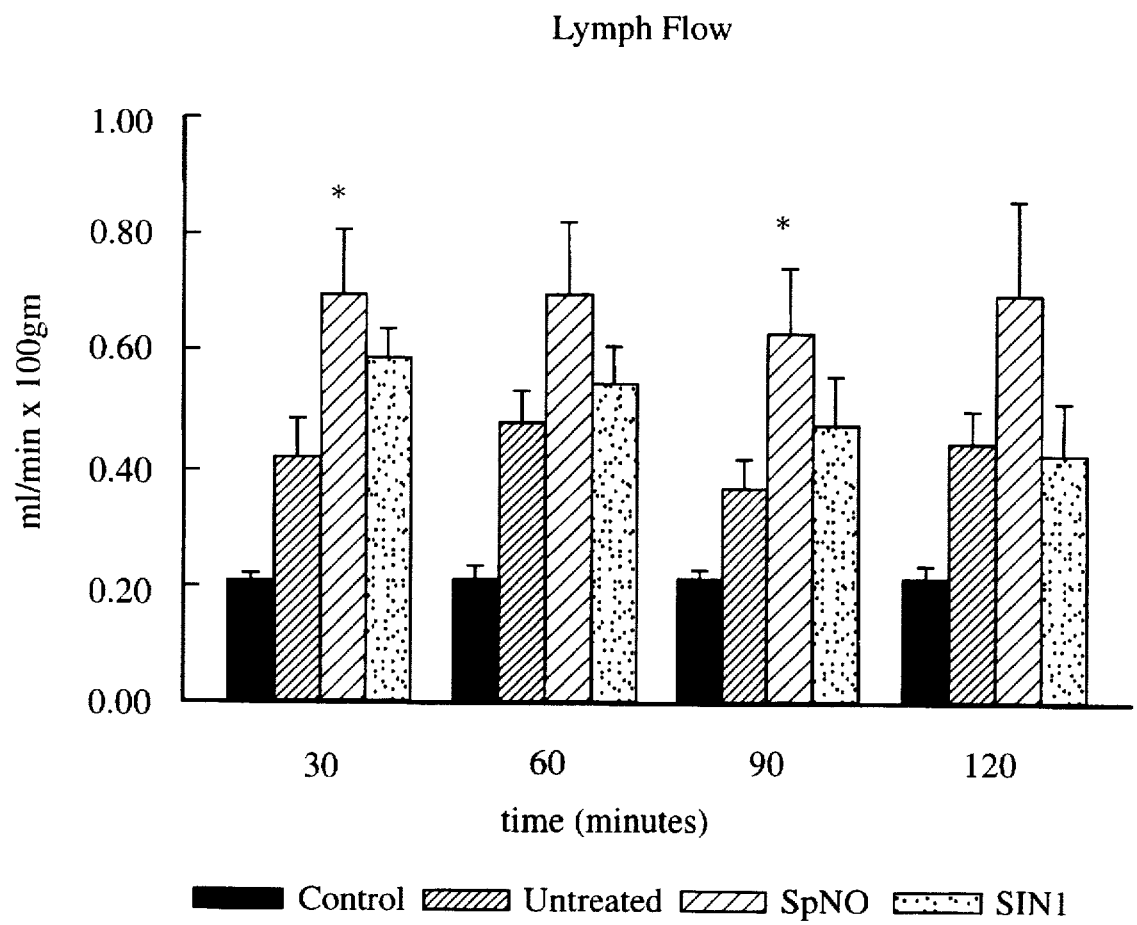
FIG. 11 is a bar graph of lymph flow (ml/min×100 g) versus time (min) for control, untreated, SpNO-treated, and SIN-1-treated animals.
Figure 12:
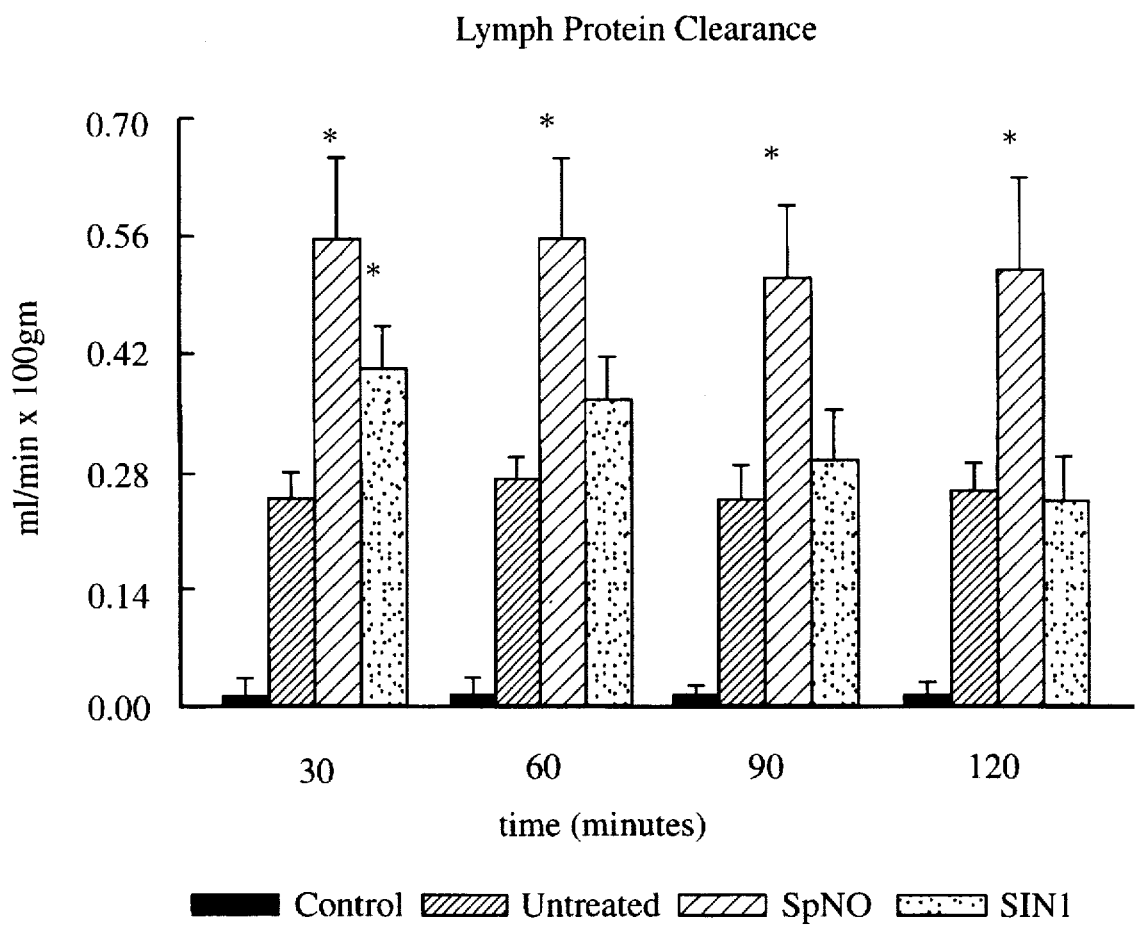
FIG. 12 is a bar graph of lymph protein clearance (ml/ min×100 g) versus time (min) for control, untreated, SpNO-treated, and SIN-1-treated animals .

Other measures of vascular permeability are lymph flow and lymph protein clearance. FIGS. 11 and 12 are bar graphs of lymph flow and lymph protein clearance (ml/min×100 g), respectively, versus time (min) for control, untreated, SpNO-treated, and SIN-1-treated animals. Error bars represent the mean ± S.D. Increased lymph flow was observed for SpNO-treated animals. This increased lymph flow was accompanied by increased lymph protein clearance, which is a measure of vascular permeability.

Figure 13:
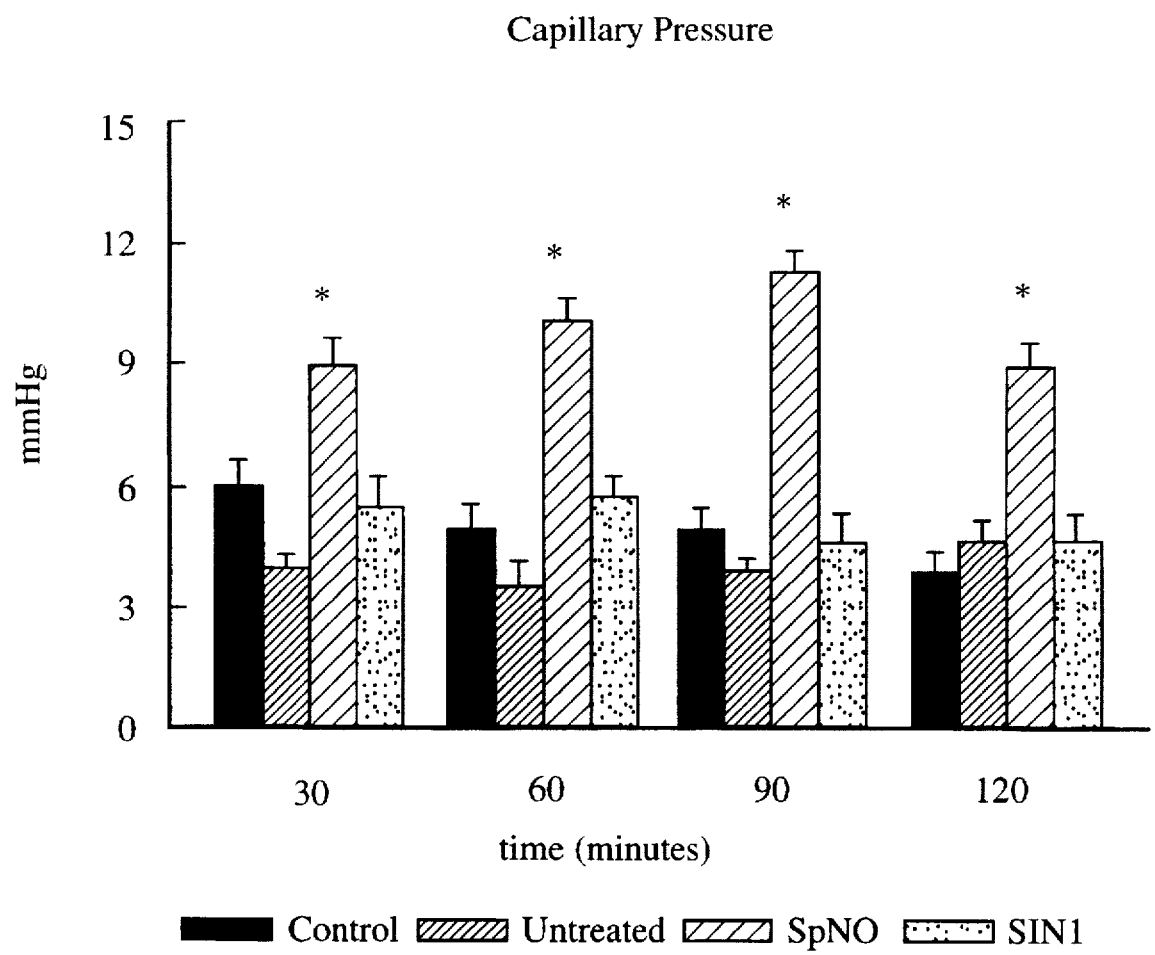
FIG. 13 is a bar graph of mm Hg versus time (min) for control, untreated, SpNO-treated, and SIN-1-treated animals.

Capillary pressure was also measured. FIG. 13 is a bar graph of mm Hg versus time (min) for control, untreated, SpNO-treated, and SIN-1-treated animals. Error bars represent the mean ± S.D. Significant elevation in capillary pressure paralleling increased lymph flow and lymph protein clearance was observed for SpNO-treated animals. No significant changes were noted in capillary pressure for SIN-1-treated animals. Total vascular resistance, however, was comparable for all groups throughout reperfusion.

All references, including publications, patents, and patent applications, cited herein are hereby incorporated by reference to the same extent as if each individual document were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A method of treating oxygen free radical induced tissue damage associated with ischemia reperfusion injury in a mammal, which method comprises administering to a mammal having ischemia reperfusion injury a treatment amount of a nitric oxide-containing compound that can spontaneously release nitric oxide under physiological conditions in the absence of oxygen, said treatment amount being sufficient to protect against oxygen free radical induced tissue damage.

2. The method of claim 1, wherein said compound is a compound of formula:

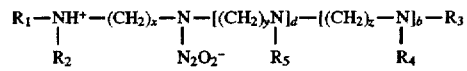

wherein b and d are independently zero or one; x, y, and z are independently 2–12; and $R_1$–$R_5$ are independently hydrogen, $C_3$–$C_8$ cycloalkyl, $C_1$–$C_{12}$ straight or branched chain alkyl, benzyl, benzoyl, phthaloyl, acetyl, trifluoroacetyl, p-toluyl, t-butoxycarbonyl or 2,2,2-trichloro-t-butoxycarbonyl.

3. The method of claim 1, wherein the ischemia reperfusion injury is associated with a condition or disease selected from the group consisting of transplantation, trauma, inflammation, stroke, seizure, rheumatoid arthritis, atherosclerosis, cancer, dementia, diabetes, hypertensive crisis, ulcers, lupus, sickle cell anemia, ischemic bowel syndrome, pulmonary emboli, Ball's syndrome, pancreatitis, heart attack, and aging.

4. The method of claim 1, wherein the compound is administered by an injection method selected from the group consisting of intravenous and local injections.

5. A method of preventing oxygen free radical induced tissue damage associated with the onset of ischemia reperfusion injury in a mammal, which method comprises administering to a mammal at immediate risk for ischemia reperfusion injury a prophylactic amount of a nitric oxide-containing compound that can spontaneously release nitric oxide under physiological conditions in the absence of oxygen, said prophylactic amount being sufficient to protect against oxygen free radical induced tissue damage.

6. The method of claim 5, wherein the ischemia reperfusion injury is associated with a condition or disease selected from the group consisting of transplantation, trauma, inflammation, stroke, seizure, rheumatoid arthritis, atherosclerosis, cancer, dementia, diabetes, hypertensive crisis, ulcers, lupus, sickle cell anemia, ischemic bowel syndrome, pulmonary emboli, Ball's syndrome, pancreatitis, heart attack, and aging.

* * * * *